(12) United States Patent
Chen et al.

(10) Patent No.: US 10,895,543 B2
(45) Date of Patent: Jan. 19, 2021

(54) WETTABILITY DETERMINATION OF ROCK SAMPLES

(71) Applicant: Saudi Arabian Oil Company, Dhahran (SA)

(72) Inventors: Quan Chen, Al Khobar (SA); Sultan Muhammad Al Enezi, Dammam (SA); Ali Abdallah Al-Yousef, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 24 days.

(21) Appl. No.: 16/420,884

(22) Filed: May 23, 2019

(65) Prior Publication Data

US 2020/0371051 A1    Nov. 26, 2020

(51) Int. Cl.
*G01N 24/08*    (2006.01)
*G01N 33/24*    (2006.01)
*G01N 13/00*    (2006.01)

(52) U.S. Cl.
CPC ........... *G01N 24/081* (2013.01); *G01N 13/00* (2013.01); *G01N 33/24* (2013.01)

(58) Field of Classification Search
CPC .. G01N 13/00; G01N 15/0852; G01N 15/088; G01N 24/081; G01N 24/082;
(Continued)

(56) References Cited

U.S. PATENT DOCUMENTS 10,287,486 B2 * 5/2019 Ayirala .................. C09K 8/594
10,422,733 B2 * 9/2019 Yang ..................... G01N 24/081
(Continued)

FOREIGN PATENT DOCUMENTS

EP    2341372    7/2011

OTHER PUBLICATIONS

Chen et al., "A mechanism study of co-current and counter-current imbibition using new magnetic resonance techniques," SCA2005-38, 2005, 16 pages.
(Continued)

*Primary Examiner* — Steven L Yeninas
(74) *Attorney, Agent, or Firm* — Fish & Richardson P.C.

(57) ABSTRACT

A primary drainage process, a core aging process, a water flooding process, an enhanced oil recovery (EOR) flooding process, and a core cleaning process is conducted on a rock sample. For each of the primary drainage process, core aging process, water flooding process, EOR flooding process, and core cleaning process, an equilibrium sample magnetization distribution and a spatially resolved spin-spin relaxation time spectrum are measured across multiple locations along a longitudinal length of the rock sample. One or more hydrocarbon saturation distributions of the rock sample are determined based on the equilibrium sample magnetization distributions. One or more wettability distributions of the rock sample are determined based on the spatially resolved spin-spin relaxation time spectrums and the one or more hydrocarbon saturation distributions. One or more wettability modification factor distributions of the rock sample are determined based on the spatially resolved spin-spin relaxation time spectrums and the hydrocarbon saturation distribution(s).

14 Claims, 11 Drawing Sheets

(58) Field of Classification Search
CPC ........ G01N 33/24; G01N 33/241; G01V 3/14; G01V 3/32; G01V 3/38; G01R 33/305; G01R 33/448; G01R 33/50
See application file for complete search history.

(56) References Cited

U.S. PATENT DOCUMENTS

| | | | | |
|---|---|---|---|---|
| 10,723,937 | B2* | 7/2020 | Ayirala | C08K 3/00 |
| 2012/0241149 | A1* | 9/2012 | Chen | G01V 3/32 |
| | | | | 166/250.01 |
| 2013/0261979 | A1* | 10/2013 | Al-Muthana | G01V 3/38 |
| | | | | 702/12 |
| 2013/0325348 | A1* | 12/2013 | Valori | G01V 3/32 |
| | | | | 702/11 |
| 2014/0340082 | A1* | 11/2014 | Yang | G01V 3/14 |
| | | | | 324/309 |
| 2016/0334346 | A1* | 11/2016 | Cao Minh | G01N 13/00 |
| 2017/0015893 | A1* | 1/2017 | Al-Yousef | C09K 8/58 |
| 2019/0346385 | A1* | 11/2019 | Reiderman | G01R 33/56 |
| 2019/0368994 | A1* | 12/2019 | Al Readean | G01N 33/241 |

OTHER PUBLICATIONS

Fu et al., "Modeling and simulation of transition zones in tight carbonate reservoirs by incorporation of improved rock typing and hysteresis models," Journal of Petroleum Exploration and Production Technology vol. 8, 2018, 18 pages.

OnePetro [online], available on or before Apr. 1, 2007, retrieved on Nov. 2, 2018, URL <https://www.onepetro.org/>, 2 pages.

Perrin et al., "Core-scale experimental study of relative permeability properties of CO2 and brine in reservoir rocks," Energy Procedia vol. 1, 2009, 8 pages.

Shi et al., "Capillary pressure and relative permeability correlations for transition zones of carbonate reservoirs," Journal of Petroleum Exploration Production and Technology, vol. 8, 2018, 18 pages.

Siqveland et al., "Aging time control by NMR relaxation," 7th International Symposium on Reservoir Wettability, Tasmania, Australia, Jan. 1991, 10 pages.

Spearing et al., "Transition Zone Behaviour: The Measurement of Bounding and Scanning Relative Permeability and Capillary Pressure Curves at Reservoir Conditions for a Giant Carbonate Reservoir," presented at the Abu Dhabi International petroleum Exhibition and Conference, Nov. 10-13, 2014, 14 pages.

Williams et al., "Application of Magnetic resonance imaging in special core analysis studies," Reviewed Proceeding 1st Soc. Core Analysts European Core Analysis Symp. Gordon and Breach London, 1990, 30 pages.

Johannesen et al., "Evaluation of wettability distributions in experimentally aged core," SCA2008-17, presented at the International Symposium of the Society of Core Analysts, Abu Dhabi, UAE, Oct. 29-Nov. 2, 2008, 12 pages.

Liang et al., "Wettability characterization of low-permeability reservoirs using nuclear magnetic resonance: an experimental study," Journal of Petroleum Science and Engineering, Mar. 2019, 178:121-132.

Mitchell et al., "Magnetic resonance imaging in laboratory petrophysical core analysis," Physics Reports, North Holland, Amsterdam, Jan. 2013, 526(3):165-225.

PCT International Search Report and Written Opinion in International Appln. No. PCT/US2020/034214, dated Sep. 2, 2020, 17 pages.

\* cited by examiner

WETTABILITY DETERMINATION OF ROCK SAMPLES

TECHNICAL FIELD

This disclosure generally relates to determining wettability of rock samples, for example, obtained from a subterranean formation.

BACKGROUND

Wettability describes the tendency of one fluid to spread on or adhere to a solid surface in the presence of other immiscible fluids. Wettability is therefore related to the interactions between fluid and solid substances. In a subterranean formation of a hydrocarbon reservoir, the solid substances include the rock mineral assemblage, and the fluid substances can include water, oil, gas, or combinations of these.

Understanding the wettability of a subterranean formation can be useful in optimizing the process of extracting hydrocarbons from the subterranean formation. Because wettability can influence not only the profile of initial hydrocarbon saturation but also the hydrocarbon extraction process, some processes (such as water flooding and enhanced oil recovery (EOR) processes) are designed to modify the wettability of the subterranean formation in such a manner to improve hydrocarbon extraction.

SUMMARY

The present disclosure describes techniques that can be used for determining wettability of a rock sample. The subject matter described in this specification can be implemented in particular implementations so as to realize one or more of the following advantages. First, a representative fluid saturation distribution and wettability distribution in the oil-water transition zone of a subterranean formation can be established using a single rock sample. Second, in-situ fluid saturation distribution measurements after primary drainage, core aging, water flooding, enhanced oil recovery (EOR) flooding, and core cleaning processes can enable the determination of initial and residual hydrocarbon saturation distributions after water flooding and after EOR flooding. Initial-residual correlations can also be determined for both the water flooding and the EOR flooding processes. Third, the use of magnetic resonance imaging (MRI) to measure in-situ wettability distributions is non-invasive and does not interfere with fluid distributions within the rock sample. MRI can be applied to monitor dynamic processes, such as primary drainage, core aging, water flooding, and EOR flooding processes. MRI can also be implemented to determine a suitable core aging time duration by monitoring the changes of the in-situ spatially resolved spin-spin relaxation time spectra during the core aging process. Fourth, in-situ spatially resolved spin-spin relaxation time spectrum measurements after primary drainage, core aging, water flooding, EOR flooding, and core cleaning processes can enable the determination of wettability distributions after each of the processes. Wettability modification factor distributions can also be determined for both the water flooding and the EOR flooding processes. Fifth, all of the aforementioned values can be determined with a single rock sample and one set of tests, which can prove to be quicker, more efficient, and more economical in comparison to running multiple tests across multiple rock samples. Furthermore, because the entire set of tests is performed on a single rock sample, the comparison of obtained data can be more straightforward and reliable than comparing data sets of different rock samples.

Certain aspects of the subject matter described here can be implemented as a method. A primary drainage process, a core aging process, a water flooding process, an enhanced oil recovery (EOR) flooding process, and a core cleaning process is conducted on a rock sample. For each of the primary drainage process, core aging process, water flooding process, EOR flooding process, and core cleaning process, an equilibrium sample magnetization distribution and a spatially resolved spin-spin relaxation time spectrum are measured across multiple locations along a longitudinal length of the rock sample. One or more hydrocarbon saturation distributions of the rock sample are determined based on the equilibrium sample magnetization distributions. One or more wettability distributions of the rock sample are determined based on the spatially resolved spin-spin relaxation time spectrums and the one or more hydrocarbon saturation distributions. One or more wettability modification factor distributions of the rock sample are determined based on the spatially resolved spin-spin relaxation time spectrums and the one or more hydrocarbon saturation distributions.

This, and other aspects, can include one or more of the following features.

The primary drainage process and the core aging process can each include flowing a hydrocarbon stream into a first end of the rock sample at a first hydrocarbon flow rate and flowing a deuterium oxide ($D_2O$) stream across a second end of the rock sample at a first $D_2O$ rate. The first hydrocarbon flow rate can be greater than the first $D_2O$ flow rate. The flows of the hydrocarbon stream and the $D_2O$ stream to the rock sample can result in a differential pressure across the longitudinal length of the rock sample.

The water flooding process can include flowing the $D_2O$ stream into the second end of the rock sample at a second $D_2O$ flow rate. The second $D_2O$ flow rate can be greater than the first $D_2O$ flow rate. The water flooding process can include reducing the flow of the hydrocarbon stream across the first end of the rock sample. The differential pressure across the longitudinal length of the rock sample during the water flooding process can be substantially equal to the differential pressure during the primary drainage process.

The EOR flooding process can include flowing an EOR stream into the second end of the rock sample. The EOR stream can have a different composition from the $D_2O$ stream. The EOR flooding process can include reducing the flow of the hydrocarbon stream across the first end of the rock sample. The differential pressure across the longitudinal length of the rock sample during the EOR flooding process can be substantially equal to the differential pressure during the water flooding process.

The core cleaning process can include flowing toluene through the rock sample, flowing methanol through the rock sample, and repeating and alternating between toluene and methanol until an effluent from the rock sample is visually clear. Once the effluent from the rock sample is visually clear, if the last fluid flowed through the rock sample was methanol, toluene can be flowed through the rock sample once more.

The core cleaning process can include measuring an equilibrium sample magnetization distribution and a spatially resolved spin-spin relaxation time spectrum across the locations along the longitudinal length of the rock sample. The core cleaning process can include flowing the hydrocarbon stream through the rock sample until the spatially resolved spin-spin relaxation time spectrum across the locations along the longitudinal length of the rock sample stabilizes.

The one or more hydrocarbon saturation distributions can include an initial hydrocarbon saturation distribution ($S_i(z)$). Determining the one or more hydrocarbon saturation distributions can include determining the initial hydrocarbon saturation distribution to be a ratio of the equilibrium sample magnetization distribution for the core aging process to the equilibrium sample magnetization distribution for the core cleaning process.

The one or more hydrocarbon saturation distributions can include a water flooding residual hydrocarbon saturation distribution ($S_{wf,r}(z)$). Determining the one or more hydrocarbon saturation distributions can include determining the water flooding residual hydrocarbon saturation distribution to be a ratio of the equilibrium sample magnetization distribution for the water flooding process to the equilibrium sample magnetization distribution for the core cleaning process.

The one or more hydrocarbon saturation distributions can include an EOR flooding residual hydrocarbon saturation distribution ($S_{EORf,r}(z)$). Determining the one or more hydrocarbon saturation distributions can include determining the EOR flooding residual hydrocarbon saturation distribution to be a ratio of the equilibrium sample magnetization distribution for the EOR flooding process to the equilibrium sample magnetization distribution for the core cleaning process.

The one or more wettability distributions can include an initial hydrocarbon wettability distribution ($W_i(z)$). Determining the one or more wettability distributions can include determining the initial hydrocarbon wettability distribution to be:

$$W_i(z) = \frac{\left[\frac{1}{T_{2,i}(z)} - \frac{1}{T_{2,B}}\right]S_i(z)}{\frac{1}{T_{2,1}(z)} - \frac{1}{T_{2,B}}},$$

where $T_{2,i}(z)$ is the spatially resolved spin-spin relaxation time spectrum for the core aging process, $T_{2,1}(z)$ is the spatially resolved spin-spin relaxation time spectrum for the core cleaning process, and $T_{2,B}$ is a bulk spin-spin relaxation time of the hydrocarbon stream.

The one or more wettability distributions can include a water flooding residual hydrocarbon wettability distribution ($W_{wf,r}(z)$). Determining the one or more wettability distributions can include determining the water flooding residual hydrocarbon wettability distribution to be:

$$W_{wf,r}(z) = \frac{\left[\frac{1}{T_{2,wf}(z)} - \frac{1}{T_{2,B}}\right]S_{wf,r}(z)}{\frac{1}{T_{2,1}(z)} - \frac{1}{T_{2,B}}},$$

where $T_{2,wf}(z)$ is the spatially resolved spin-spin relaxation time spectrum for the water flooding process, $T_{2,1}(z)$ is the spatially resolved spin-spin relaxation time spectrum for the core cleaning process, and $T_{2,B}$ is a bulk spin-spin relaxation time of the hydrocarbon stream.

The one or more wettability distributions can include an EOR flooding residual hydrocarbon wettability distribution ($W_{EORf,r}(z)$). Determining the one or more wettability distributions can include determining the EOR flooding residual hydrocarbon wettability distribution to be:

$$W_{EORf,r}(z) = \frac{\left[\frac{1}{T_{2,EORf}(z)} - \frac{1}{T_{2,B}}\right]S_{EORf,r}(z)}{\frac{1}{T_{2,1}(z)} - \frac{1}{T_{2,B}}},$$

where $T_{2,EORf}(z)$ is the spatially resolved spin-spin relaxation time spectrum for the EOR flooding process, $T_{2,1}(z)$ is the spatially resolved spin-spin relaxation time spectrum for the core cleaning process, and $T_{2,B}$ is a bulk spin-spin relaxation time of the hydrocarbon stream.

The one or more wettability modification factor distributions can include a water flooding wettability modification factor distribution ($WMF_{wf}(z)$). Determining the one or more wettability modification factor distributions can include determining the water flooding wettability modification factor distribution to be:

$$WMF_{wf}(z) = \frac{\left[\frac{1}{T_{2,wf}(z)} - \frac{1}{T_{2,B}}\right]S_{wf,r}(z)}{\left[\frac{1}{T_{2,i}(z)} - \frac{1}{T_{2,B}}\right]S_i(z)},$$

where $T_{2,wf}(z)$ is the spatially resolved spin-spin relaxation time spectrum for the water flooding process, $T_{2,i}(z)$ is the spatially resolved spin-spin relaxation time spectrum for the core aging process, and $T_{2,B}$ is a bulk spin-spin relaxation time of the hydrocarbon stream.

The one or more wettability modification factor distributions can include an EOR wettability modification factor distribution ($WMF_{EORf}(z)$). Determining the one or more wettability modification factor distributions can include determining the EOR flooding wettability modification factor distribution to be:

$$WMF_{EORf}(z) = \frac{\left[\frac{1}{T_{2,EORf}(z)} - \frac{1}{T_{2,B}}\right]S_{EORf,r}(z)}{\left[\frac{1}{T_{2,wf}(z)} - \frac{1}{T_{2,B}}\right]S_{wf,r}(z)},$$

where $T_{2,EORf}(z)$ is the spatially resolved spin-spin relaxation time spectrum for the EOR flooding process, $T_{2,wf}(z)$ is the spatially resolved spin-spin relaxation time spectrum for the water flooding process, and $T_{2,B}$ is a bulk spin-spin relaxation time of the hydrocarbon stream.

Certain aspects of the subject matter described can be implemented as a system configured to implement any one of the methods described above.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DETAILED DESCRIPTION

This disclosure describes determining wettability of a rock sample, for example, obtained from a subterranean formation. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

Wettability of an ideal solid surface by a liquid can be characterized by the contact angle between the surface and a droplet of the liquid on the surface. The contact angle of a sessile liquid drop on a smooth homogeneous horizontal solid surface is controlled by the thermodynamic equilibrium of the liquid drop under the action of three interfacial tensions: solid-liquid interfacial tension, solid-vapor interfacial tension, and liquid-vapor interfacial tension. The relationship between contact angle and the three interfacial tensions can be described by Young's equation. A contact angle of 0 degrees (°) means that the solid surface is completely wetted by the liquid. A contact angle between 0° and 90° can indicate that the wetting of the solid surface by the liquid is favorable. A contact angle greater than 90° can indicate that the wetting of the solid surface by the liquid is unfavorable. The characterization of wettability for a hydrocarbon reservoir, however, is more complicated than an ideal solid surface due to the complexities of reservoir rocks, fluids, and their interactions in a reservoir system.

In some oil and gas applications, it can be desirable to alter the wettability of a subterranean formation in order to improve production from a well that has been drilled into the subterranean formation. The wettability of the subterranean formation (for example, in its current state) should be determined in order to develop a suitable treatment that will favorably alter the wettability of the subterranean formation such that production can be improved.

Figure 1:
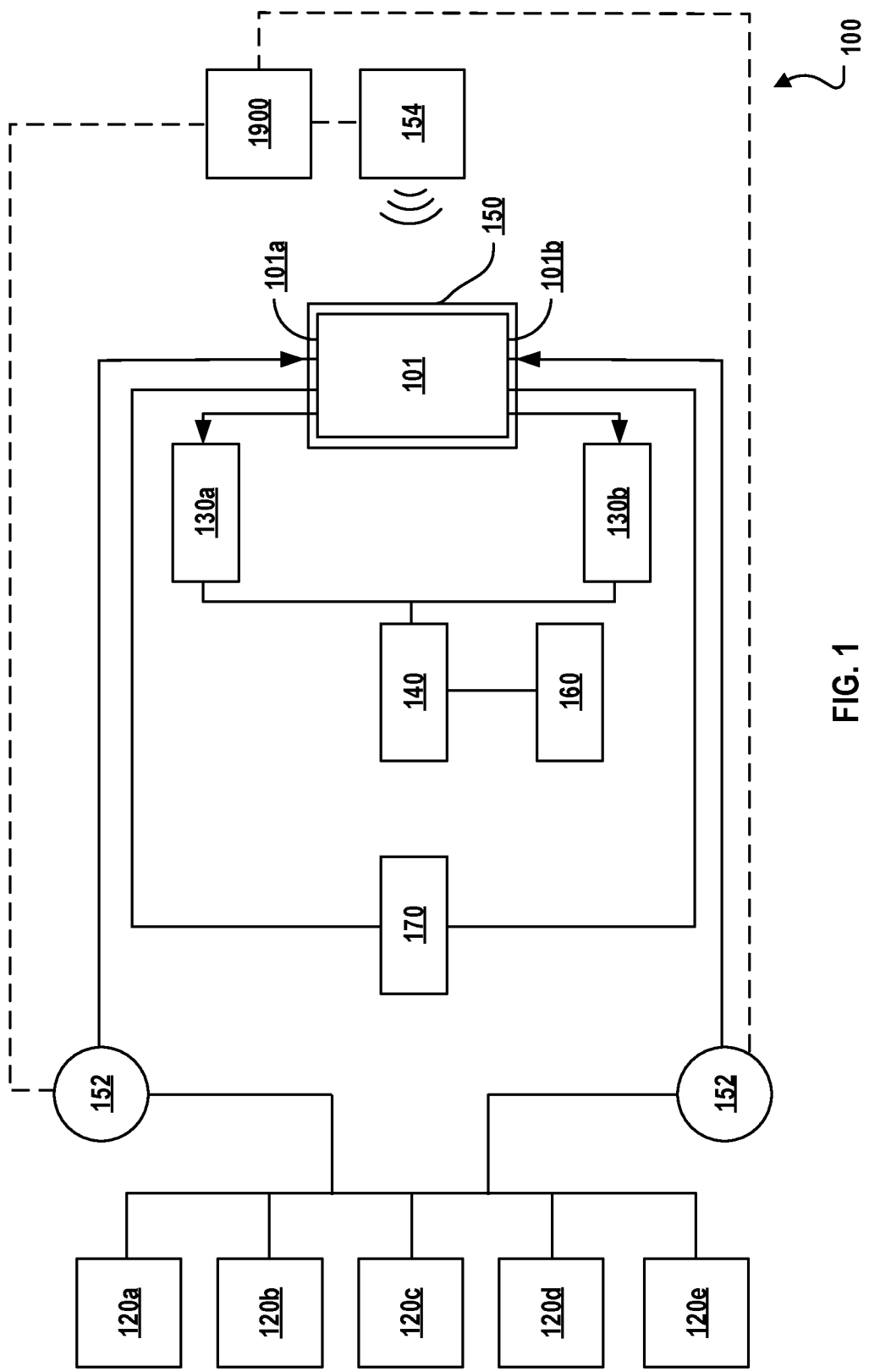
FIG. 1 is a schematic diagram of an example system that can be used to determine a wettability of a rock sample.

FIG. 1 is an example system 100 that can be used to determine a wettability of a rock sample 101. The system 100 can include a rock sample holder 150, a hydrocarbon stream source 120a, a deuterium oxide (D$_2$O) stream source 120b, an enhanced oil recovery (EOR) stream source 120c, a toluene stream source 120d, a methanol stream source 120e, injection pumps 152, flow control valves 130a and 130b, a backpressure regulator 140, an effluent collection and measurement system 160, a differential pressure measurement system 170, and a magnetic resonance imaging (MRI) machine 154. The rock sample 101 can be held by the sample holder 150, for example, in a vertical orientation. The sample holder 150 is made of a material that is suitable for magnetic resonance imaging (MRI) applications. For example, the sample holder 150 can be made of glass fiber and polyether ether ketone (PEEK) composite. The flow control valves 130a and 130b can be used to control fluid flow to and from the rock sample 101. For example, control valve 130a can be designated for controlling fluid flow into and out of the first end 101a of the rock sample 101, and control valve 130b can be designated for controlling fluid flow into and out of the second end 101b of the rock sample 101. The backpressure regulator 140 can be used to control backpressure in the system 100. Backpressure is the pressure downstream of the rock sample 101. For example, the backpressure regulator 140 can be used to maintain a constant backpressure in the system 100. The effluent collection and measurement system 160 can be used to collect and measure the effluent from the rock sample 101. The differential pressure measurement system 170 can be used to measure the differential pressure across the rock sample 101. The differential pressure measurement system 170 can include multiple differential pressure transducers, for example, with various differential pressure ranges. The various differential pressure transducers can be connected to each end (101a and 101b) of the rock sample 101.

In some implementations, the injection pump 152 can be connected to each of the hydrocarbon stream source 120a, the D$_2$O stream source 120b, the EOR stream source 120c, the toluene stream source 120d, and the methanol stream source 120e. In some implementations, the system 100 includes additional injection pumps 152, and each of the injection pumps 152 are designated for one of the sources 120a, 120b, 120c, 120d, or 120e. In some implementations, the system 100 includes one additional injection pump 152, and each of the injection pumps 152 is designated for flowing fluid to one of the ends of the rock sample 101. For example, one injection pump 152 can be designated for flowing fluid to a first end 101a of the rock sample 101, and the other injection pump 152 can be designated for flowing fluid to a second end 101b of the rock sample 101. In such implementations, each of the injection pumps 152 can be connected to each of the sources 120a, 120b, 120c, 120d, and 120e. In some implementations, after fluid phase separation, effluent from the rock sample 101 is recycled to one of the sources 120a, 120b, or 120c. In some implementations, effluent from the rock sample 101 is collected and subsequently measured by the effluent collection and measurement system 160.

The system 100 can include a computer 1900 to perform operations, such as controlling one or more of the components of the system 100 (for example, the injection pump 152 and the MRI machine 154) and performing calculations. The computer 1900 is described in more detail later in relation to FIG. 19.

Figure 2:
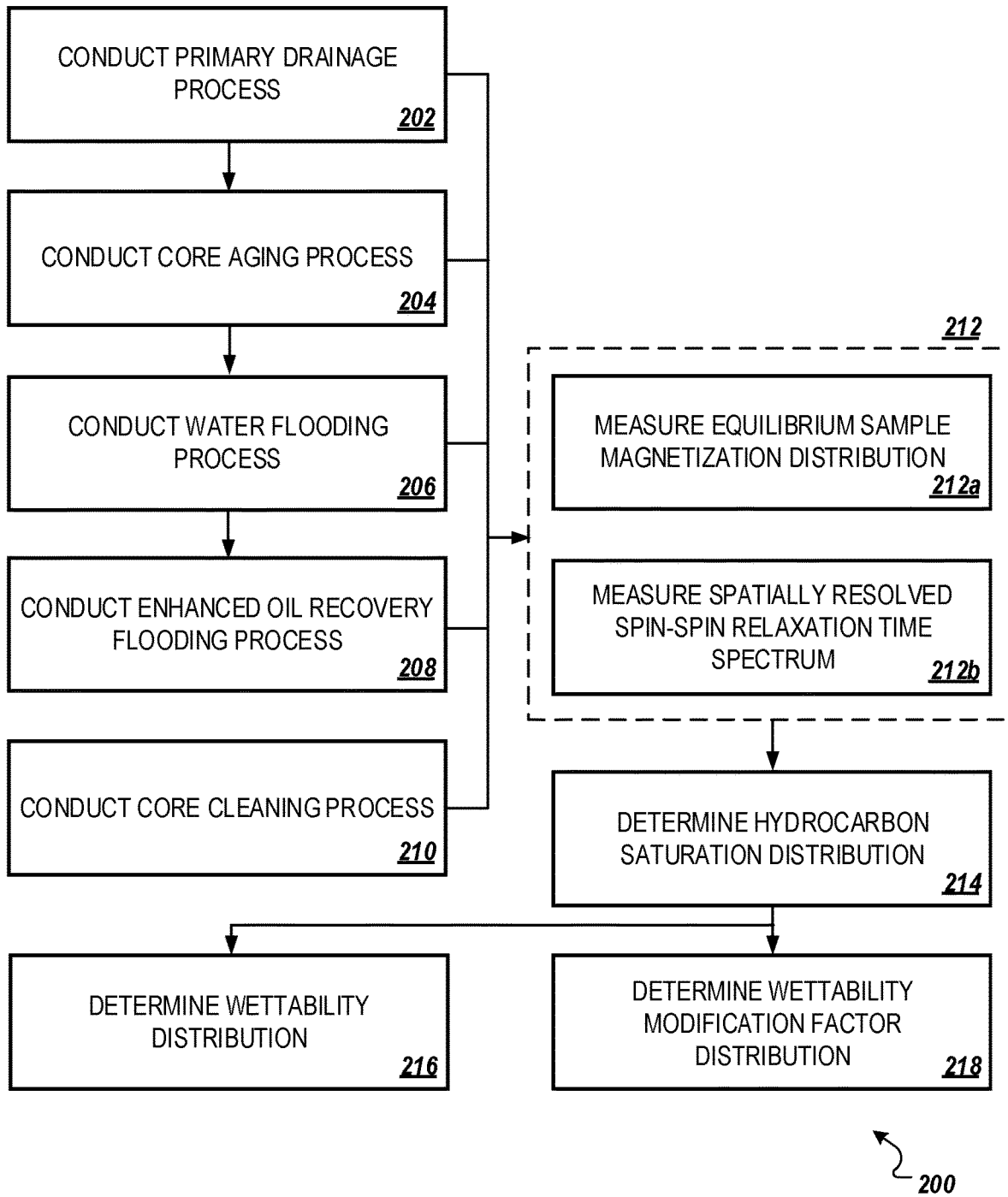
FIG. 2 is a flowchart of an example method for determining a wettability of a rock sample.

FIG. 2 is a flowchart of an example method 200 for determining a wettability of a rock sample (such as the rock sample 101). For clarity of presentation, the description that follows generally describes method 200 in the context of the other figures in this description (for example, the method 200 can be implemented using the system 100). However, it will be understood that method 200 can be performed, for example, by any suitable system, environment, software, and hardware, or a combination of systems, environments, software, and hardware, as appropriate. In some implementations, various steps of method 200 can be run in parallel, in combination, in loops, or in any order.

In an oil-water transition zone of a subterranean formation, the initial water saturation can be derived from the balance between gravity and capillary forces, as a function of height above the free water level. The balance between gravity and capillary forces is shown in Equation 1:

$$P_c = (\rho_w - \rho_o)gh \qquad (1)$$

where $P_c$ is capillary pressure (for example, in pascal (Pa)), $\rho_w$ is the density of water (for example, in kilogram per cubic meter (kg/m$^3$)), $\rho_o$ is the density of oil (for example, in kg/m$^3$), g is the acceleration of gravity (for example, in meters per square seconds (m/s$^2$)), and h is the height above the free water level (for example, in meters (m)).

Capillary pressure ($P_c$) is also defined as the equilibrium pressure difference between an oil phase and a water phase, and this definition is shown in Equation 2:

$$P_c = P_o - P_w \qquad (2)$$

where $P_o$ is the pressure of the oil phase (for example, in Pa), and $P_w$ is the pressure of the water phase (for example, in Pa).

Equations 1 and 2 can be combined to form Equation 3:

$$P_o = (\rho_w - \rho_o)gh + P_w \qquad (3)$$

At step 202, a primary drainage process is conducted on the rock sample 101. In some implementations, the rock sample 101 is already fully saturated with D$_2$O. The primary drainage process can include flowing a hydrocarbon stream into the first end 101a of the rock sample 101 at a first hydrocarbon flow rate. In some implementations, the control valve 130a is closed, and the control valve 130b is open during the primary drainage process at step 202. The hydrocarbon stream can flow into the first end 101a of the rock sample 101 at a constant pressure ($P_o$) by one of the pumps 152 operating under a constant pressure delivery mode. The constant pressure ($P_o$) can be determined by Equation 3 and can be equal to the hydrocarbon phase pressure at the top of an oil-water transition zone of a hydrocarbon reservoir. The hydrocarbon stream includes at least one hydrocarbon. The hydrocarbon stream can include, for example, crude oil obtained from the same formation as the rock sample 101. In some implementations, the constant pressure ($P_o$) is in a range of from approximately 1 megaPascal (MPa) to approximately 50 MPa. In some implementations, the corresponding first hydrocarbon flow rate at constant pressure ($P_o$) is in a range of from approximately 2 milliliters per hour (mL/hr) to approximately 1,000 mL/hr. The primary drainage process can include washing the second end 101b of the rock sample 101 by flowing a D$_2$O stream across the second end 101b of the rock sample 101 at a first D$_2$O flow rate. The D$_2$O stream includes D$_2$O. The D$_2$O stream can include additional components, such as a salt. For example, the D$_2$O stream can include sodium chloride, potassium chloride, calcium chloride, magnesium chloride, sodium bicarbonate, sodium sulfate, or combinations of these. The first D$_2$O flow rate can be less than the first hydrocarbon flow rate. In some implementations, the first D$_2$O is in a range of from approximately 1 mL/hr to approximately 100 mL/hr. Effluent from the second end 101b of the rock sample 101 can include D$_2$O from the D$_2$O stream washing the second end 101b, D$_2$O that originally saturated the rock sample 101, and hydrocarbon from the hydrocarbon stream flowed to the first end 101a. The effluent from the second end 101b of the rock sample 101 can flow out through the control valve 130b and backpressure regulator 140. The backpressure ($P_w$) can be controlled and maintained by the backpressure regulator 140.

The flow of the hydrocarbon stream into the first end 101a of the rock sample 101 at step 202 can be provided at a pressure equal to $P_o$ (as provided in Equation 3). The flow of the D$_2$O stream across the second end 101b of the rock sample 101 at step 202 can be provided at a pressure equal to $P_w$.

Flowing the hydrocarbon stream into the first ends 101a of the rock sample 101 and washing the second end 101b of the rock sample 101 with the D$_2$O stream can result in a differential pressure across the longitudinal length of the rock sample 101. For example, the differential pressure resulting from the flows of the hydrocarbon stream and the D$_2$O stream can be in a range of from approximately 1,000 Pascals (Pa) to approximately 20 MPa. The flow of the hydrocarbon stream and the D$_2$O stream to the rock sample 101 can continue until the fluid saturation distribution along a longitudinal length of the rock sample 101 stabilizes.

At step 204, a core aging process is conducted on the rock sample 101. The core aging process at step 204 is essentially a continuation of the primary drainage process at step 202. The core aging process can include continuing the flow of the hydrocarbon stream to the first end 101a of the rock sample 101. The core aging process can include continuing the flow of the D₂O stream across the second end 101b of the rock sample 101. The differential pressure across the longitudinal length of the rock sample 101 can be maintained during step 204. In some implementations, the differential pressure across the longitudinal length of the rock sample 101 is maintained at step 204 to be the same as the differential pressure across the longitudinal length of the rock sample 101 at step 202. The core aging process at step 204 allows microscopic redistribution of hydrocarbon and D₂O stream at the rock pore surface. In doing so, a fluid saturation and wettability distribution representative of an oil-water transition of the reservoir can be restored. The core aging process at step 204 can continue until the fluid saturations and spatially resolved spin-spin relaxation time spectra along the longitudinal length of the rock sample 101 stabilizes (that is, does not change with time).

At steady state equilibrium, a balance between capillary pressure ($P_c$) and viscous forces along the longitudinal length of the rock sample 101 is achieved (as defined by Equation 2). The effects of viscous forces imposed by the oil phase pressure ($P_o$) and water phase pressure ($P_w$) act equivalently as gravity in the oil-water transition zone of a subterranean formation (as defined by Equation 1). The primary drainage process of step 202 and the core aging process of step 204 allow the rock sample 101 to represent the initial water and hydrocarbon saturation of a reservoir as a function of height (along the longitudinal length of the rock sample 101) above free water level (FWL) in the oil-water transition zone. The duration of the core aging process at step 204 is called core aging time. The core aging time can dependent on the source reservoir of the rock sample 101 and the fluids used. The core aging time can vary from approximately 1 week to a few months. The spatially resolved spin-spin relaxation time spectrum monitoring by MRI allows for determination of the core aging time necessary to restore reservoir-representative wettability distribution.

At step 206, a water flooding process is conducted on the rock sample 101. The water flooding process can include flowing the D₂O stream into the second end 101b of the rock sample 101 at a second D₂O flow rate. In some implementations, the control valve 130a is open, and the control valve 130b is closed during the water flooding process at step 206. The second D₂O flow rate at step 206 can be greater than the first D₂O flow rate of step 202. In some implementations, the second D₂O flow rate is in a range of from approximately 2 mL/hr to approximately 1,000 mL/hr. The water flooding process can include washing the first end 101a of the rock sample 101 by flowing the hydrocarbon stream across the first end 101a of the rock sample. The flow of the hydrocarbon stream across the first end 101a of the rock sample 101 can be reduced (in comparison to the flow provided in steps 202 and 204). In some implementations, the flow of the hydrocarbon stream to the first end 101a of the rock sample 101 is stopped at step 206 (that is, no flow of hydrocarbon is provided to the rock sample 101). The flow of the D₂O stream into the second end 101b of the rock sample 101 can cause D₂O and hydrocarbon (that was already present in the rock sample 101 at the beginning of step 206) to exit the rock sample 101 from the first end 101a. Effluent from the first end 101a of the rock sample 101 can therefore include D₂O from the D₂O stream flowed into the second end 101b, hydrocarbon that was originally in the rock sample 101 after step 204 and before step 206, and hydrocarbon from the hydrocarbon stream washing the first end 101a. The effluent from the first end 101a of the rock sample 101 can flow out through the control valve 130a and backpressure regulator 140. The backpressure ($P_w$) can be controlled and maintained by the backpressure regulator 140.

The differential pressure across the longitudinal length of the rock sample 101 can be maintained during step 206. In some implementations, the differential pressure across the longitudinal length of the rock sample 101 is maintained at step 206 to be the same as the differential pressure across the longitudinal length of the rock sample 101 at step 202, at step 204, or any combination of these. The flow of the D₂O stream into the second end 101b of the rock sample 101 can continue until additional hydrocarbon stops being produced from the rock sample 101 (that is, no more hydrocarbon exits the rock sample 101). Some hydrocarbon can still be present in the rock sample 101 at the end of step 206, and further injection of the D₂O stream may not cause the hydrocarbon to be produced from the rock sample 101. Injection of another fluid at step 208 can cause at least a portion of the remaining hydrocarbon to be produced from the rock sample 101.

At step 208, an enhanced oil recovery (EOR) flooding process is conducted on the rock sample 101. The EOR process at step 208 is similar to the water flooding process at step 206, except that an EOR stream is used instead of the D₂O stream. In some implementations, the control valve 130a is open, and the control valve 130b is closed during the EOR flooding process at step 208. The EOR flooding process can include flowing an EOR stream into the second end 101b of the rock sample 101. The EOR stream has a different composition from the D₂O stream. Although the EOR stream and the D₂O stream have different compositions, each of them can include some of the same components. For example, the EOR stream can include D₂O. For example, the EOR stream can include one or more salts. For example, the EOR stream can be the D₂O stream which has been altered to include additional salt content. In some implementations, the EOR stream includes a surfactant, a polymer, an alkali, a nanoparticle, a chemical additive, or any combination of these. The flow rate of the EOR stream at step 208 can be the same as the second D₂O flow rate of step 206. In some implementations, the flow rate of the EOR stream is in a range of from approximately 2 mL/hr to approximately 1,000 mL/hr. The flow of the hydrocarbon stream across the first end 101a of the rock sample 101 can be similar or the same as that of step 206. In some implementations, the flow of the hydrocarbon stream across the first end 101a of the rock sample 101 is stopped at step 208 (that is, no flow of the hydrocarbon stream is provided to the rock sample 101). The flow of the EOR stream into the second end 101b of the rock sample 101 can cause hydrocarbon (that was already present in the rock sample 101 at the beginning of step 208) to exit the rock sample 101 from the first end 101a.

The differential pressure across the longitudinal length of the rock sample 101 can be maintained during step 208. In some implementations, the differential pressure across the longitudinal length of the rock sample 101 is maintained at step 208 to be the same as the differential pressure across the longitudinal length of the rock sample 101 at step 202, at step 204, at step 206, or any combination of these. The flow of the EOR stream into the second end 101b of the rock sample 101 can continue until additional hydrocarbon stops being produced from the rock sample 101 (that is, no more hydrocarbon exits the rock sample 101). Some hydrocarbon can still be present in the rock sample 101 at the end of step 208, and further injection of the EOR stream may not cause the hydrocarbon to be produced from the rock sample 101.

At step 210, a core cleaning process is conducted on the rock sample 101. The core cleaning process can include flowing toluene through the rock sample 101. Toluene can be flowed through the rock sample at a flow rate in a range of approximately 1 mL/hr to approximately 1,000 mL/hr. In some implementations, toluene is flowed to the rock sample 101 for at least 1 hour. In some implementations, at least 5 pore volumes of toluene is flowed through the rock sample 101. The core cleaning process can include flowing methanol through the rock sample 101. Methanol can be flowed through the rock sample at a flow rate in a range of approximately 1 mL/hr to approximately 1,000 mL/hr. In some implementations, methanol is flowed through the rock sample 101 for at least 1 hour. In some implementations, at least 5 pore volumes of methanol is flowed through the rock sample 101. The core cleaning process can include alternating between flowing toluene and flowing methanol through the rock sample 101 until the effluent from the rock sample 101 becomes visually clear. Once the effluent from the rock sample 101 is visually clear, if the last fluid flowed through the rock sample 101 was methanol, toluene can be flowed through the rock sample 101 once more.

The core cleaning process can include a second core aging process. The second core aging process can include flowing the hydrocarbon stream through the rock sample 101. The hydrocarbon stream can be flowed through the rock sample 101 until the spatially resolved spin-spin relaxation time spectra along the longitudinal length of the rock sample 101 stabilizes (that is, does not change with time). The hydrocarbon stream can be flowed through the rock sample 101 during the second core aging process at a flow rate in a range of from approximately 1 mL/hr to approximately 100 mL/hr. The differential pressure across the longitudinal length of the rock sample 101 can be maintained during step 210. In some implementations, the differential pressure across the longitudinal length of the rock sample 101 is maintained at step 210 to be the same as (or less than) the differential pressure across the longitudinal length of the rock sample 101 at step 202, at step 204, at step 206, at step 208, or any combination of these.

For each of the steps 202, 204, 206, 208, and 210, the method 200 proceeds to step 212 (which includes sub-steps 212a and 212b). At step 212a, an equilibrium sample magnetization distribution is measured across multiple locations along a longitudinal length of the rock sample 101. The equilibrium sample magnetization distribution is measured to determine a fluid saturation distribution across the rock sample 101. During the measurement of the equilibrium sample magnetization distribution, a spin density imaging pulse sequence is applied by the Mill machine 154. As a result, hydrogen (H$^1$) nuclei (present in the fluids that fill the pore spaces of the rock sample 101) in the strong, static magnetic field are perturbed by a weak oscillating magnetic field, thereby inducing an electromagnetic signal, which is received and processed by the MRI machine 154, to obtain a spin density image of the rock sample 101. D$_2$O is invisible to magnetic resonance imaging (MRI), so the magnetic resonance signals can be attributed to the one or more hydrocarbons present in the rock sample 101.

At step 212b, a spatially resolved spin-spin relaxation time spectrum is measured across multiple locations along the longitudinal length of the rock sample 101. The spatially resolved spin-spin relaxation time spectrum is measured to determine a wettability distribution across the rock sample 101. During the measurement of the spatially resolved spin-spin relaxation time spectrum, a spin-spin relaxation time imaging pulse sequence is applied by the Mill machine 154. As a result, hydrogen (H$^1$) nuclei (present in the fluids that fill the pore spaces of the rock sample 101) in the strong, static magnetic field are perturbed by a weak oscillating magnetic field, thereby inducing an electromagnetic signal, which is received and processed by the Mill machine 154 to obtain the spatially resolved spin-spin relaxation time spectrum of the rock sample 101

At step 214, one or more hydrocarbon saturation distributions of the rock sample 101 are determined based on the equilibrium sample magnetization distributions measured at step 212a. The one or more hydrocarbon saturation distributions of the rock sample 101 determined at step 214 can include an initial hydrocarbon saturation distribution, $S_i(z)$, where z is the location along the longitudinal length L of the rock sample 101. The initial hydrocarbon saturation distribution ($S_i(z)$) can be determined based on the equilibrium sample magnetization distributions measured at step 212a for the core aging process (204) and the second core aging process of the core cleaning process (210). The initial hydrocarbon saturation distribution ($S_i(z)$) can be calculated by Equation 4:

$$S_i(z) = \frac{M_i(z)}{M_o(z)} \quad (4)$$

where $M_i(z)$ is the equilibrium sample magnetization distribution measured for the initial hydrocarbon saturation distribution at the end of the core aging process of step 204, and $M_o(z)$ is the equilibrium sample magnetization distribution measured for the full hydrocarbon saturation distribution at the end of the second core aging process of step 210.

Figure 3:
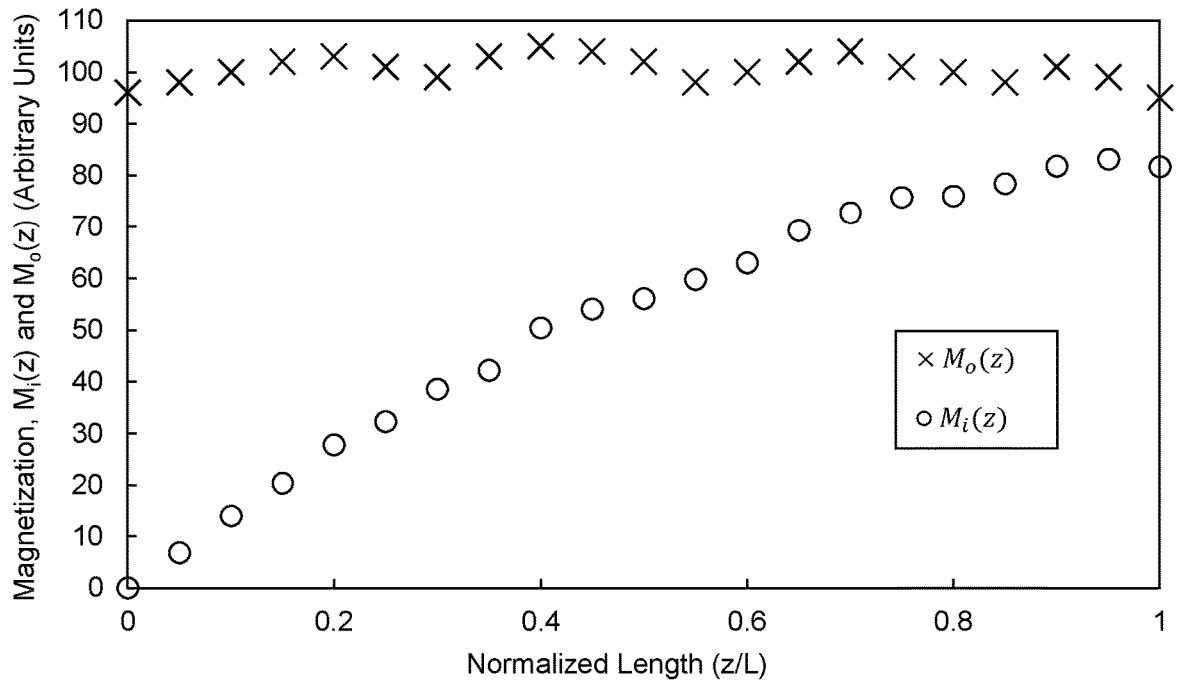
FIG. 3 is a graph showing equilibrium sample magnetization distributions for initial hydrocarbon saturation distribution and final hydrocarbon saturation distribution along a normalized length of a rock sample.
Figure 4:
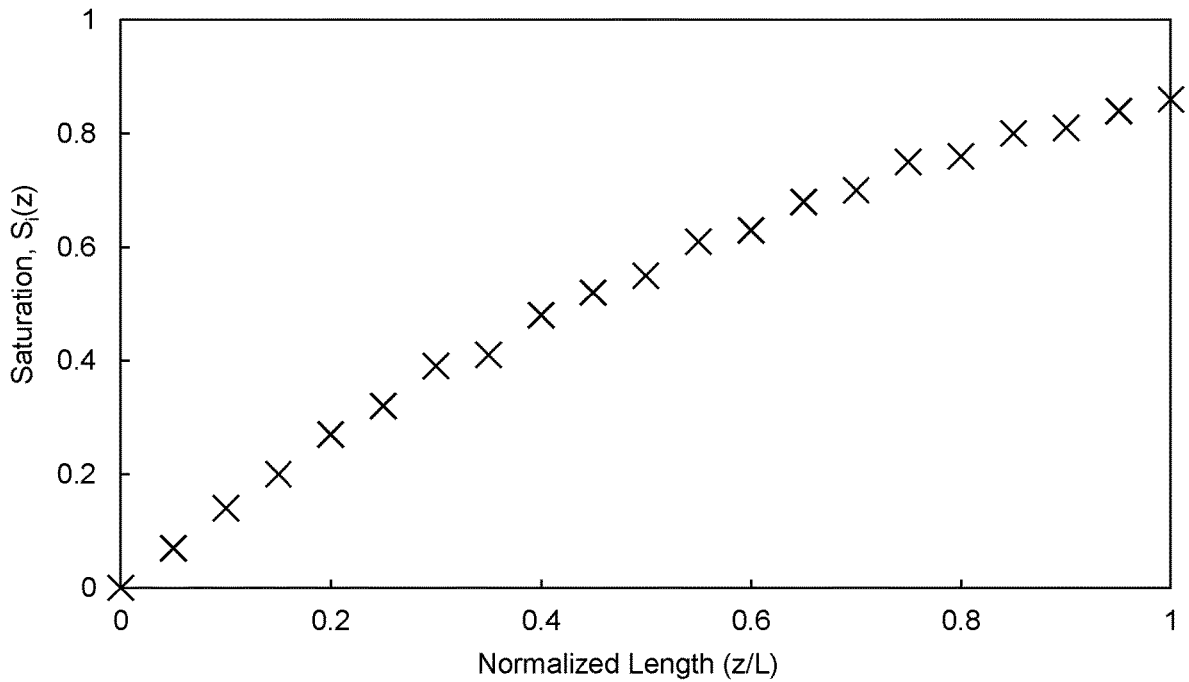
FIG. 4 is a graph showing the initial hydrocarbon saturation distribution along the normalized length of the rock sample.

FIG. 3 is a graph showing an equilibrium sample magnetization distribution $M_i(z)$ for an initial hydrocarbon saturation distribution along a normalized length (z/L) of the rock sample 101 at the end of the core aging process of step 204. FIG. 3 also shows an equilibrium sample magnetization distribution $M_o(z)$ for a final hydrocarbon saturation distribution along the normalized length of the rock sample 101 at the end of the second core aging process of step 210. FIG. 4 is a graph showing the initial hydrocarbon saturation distribution ($S_i(z)$, calculated by Equation 4) along the normalized length of the rock sample 101.

The one or more hydrocarbon saturation distributions of the rock sample 101 determined at step 214 can include a water flooding residual hydrocarbon saturation distribution, $S_{wf,r}(z)$. The water flooding residual hydrocarbon saturation distribution ($S_{wf,r}(z)$) can be determined based on the equilibrium sample magnetization distributions measured at step 212a for the water flooding process (206) and the core cleaning process (210). The water flooding residual hydrocarbon saturation distribution ($S_{wf,r}(z)$) can be calculated by Equation 5:

$$S_{wf,r}(z) = \frac{M_{wf,r}(z)}{M_o(z)} \quad (5)$$

where $M_{wf,r}(z)$ is the equilibrium sample magnetization distribution measured for the residual hydrocarbon saturation distribution at the end of the water flooding process of step 206.

Figure 5:
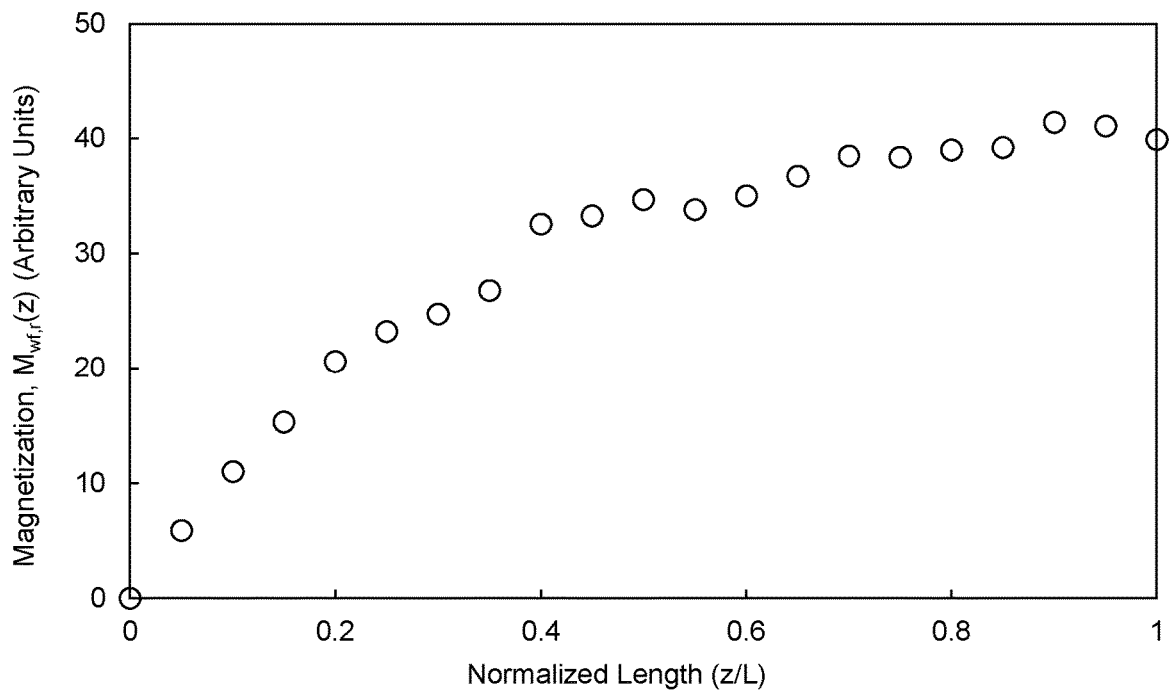
FIG. 5 is a graph showing an equilibrium sample magnetization distribution for a water flooding residual hydrocarbon saturation distribution along the normalized length of the rock sample.
Figure 6:
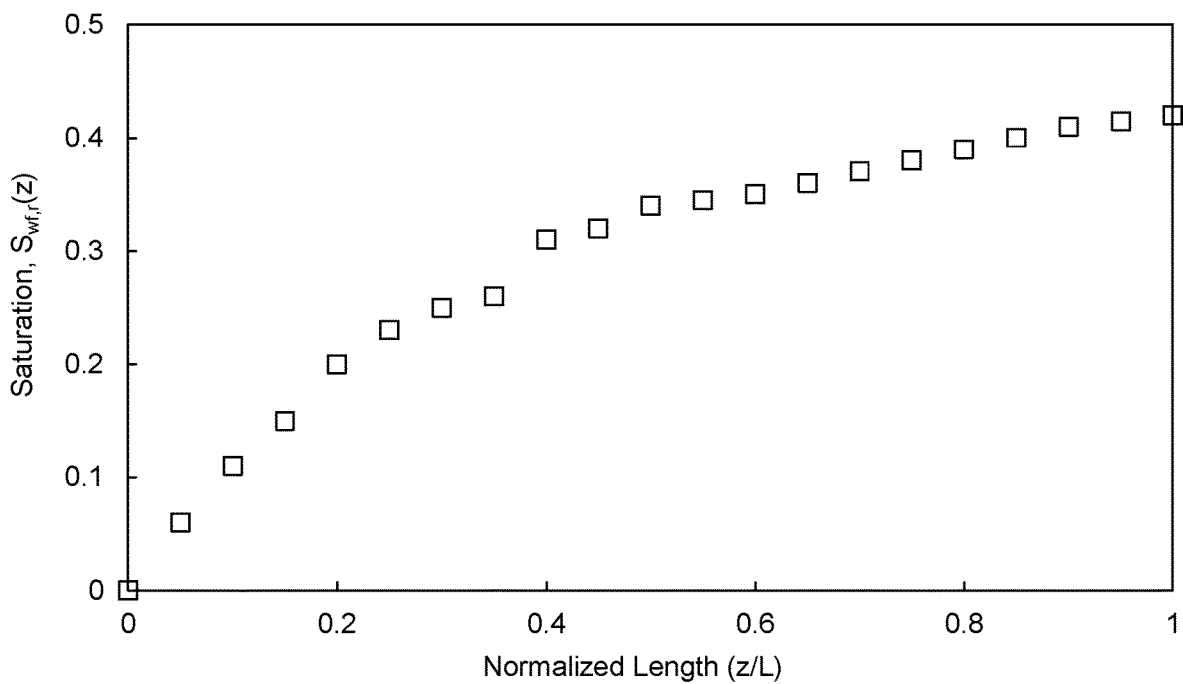
FIG. 6 is a graph showing the water flooding residual hydrocarbon saturation distribution along the normalized length of the rock sample.

FIG. 5 is a graph showing the equilibrium sample magnetization distribution $M_{wf,r}(z)$ for the water flooding residual hydrocarbon saturation distribution along the normalized length of the rock sample 101 at the end of the water flooding process of step 206. FIG. 6 is a graph showing the water flooding residual hydrocarbon saturation distribution ($S_{wf,r}(z)$, calculated by Equation 5) along the normalized length of the rock sample 101. The amount of hydrocarbons recoverable from the rock sample 101 due to water flooding is proportional to the difference between the initial hydrocarbon saturation and the residual hydrocarbon saturation for the water flooding process. Traditional methods for estimating recoverable hydrocarbon volumes in an oil-water transition zone are typically based on the assumption of a constant residual hydrocarbon saturation. The constant hydrocarbon saturation is also typically measured with a rock sample at initial hydrocarbon saturation of an oil column above the transition zone. FIG. 6 shows, however, that water flooding residual hydrocarbon saturation in the oil column (where z/L=1) is 0.42 and that residual hydrocarbon saturation in the transition zone is not constant but decreases gradually with depth. As a result, the amount of recoverable hydrocarbons and hydrocarbon reserves in the transition zone can potentially be underestimated by traditional methods.

The empirical initial-residual saturation correlation for the water flooding process (206) can be established by combining initial hydrocarbon saturation distribution ($S_i(z)$) with the water flooding residual hydrocarbon saturation distribution ($S_{wf,r}(z)$). For example, individual saturation values can be compared for the same location z along the longitudinal length L of the rock sample 101.

Figure 7:
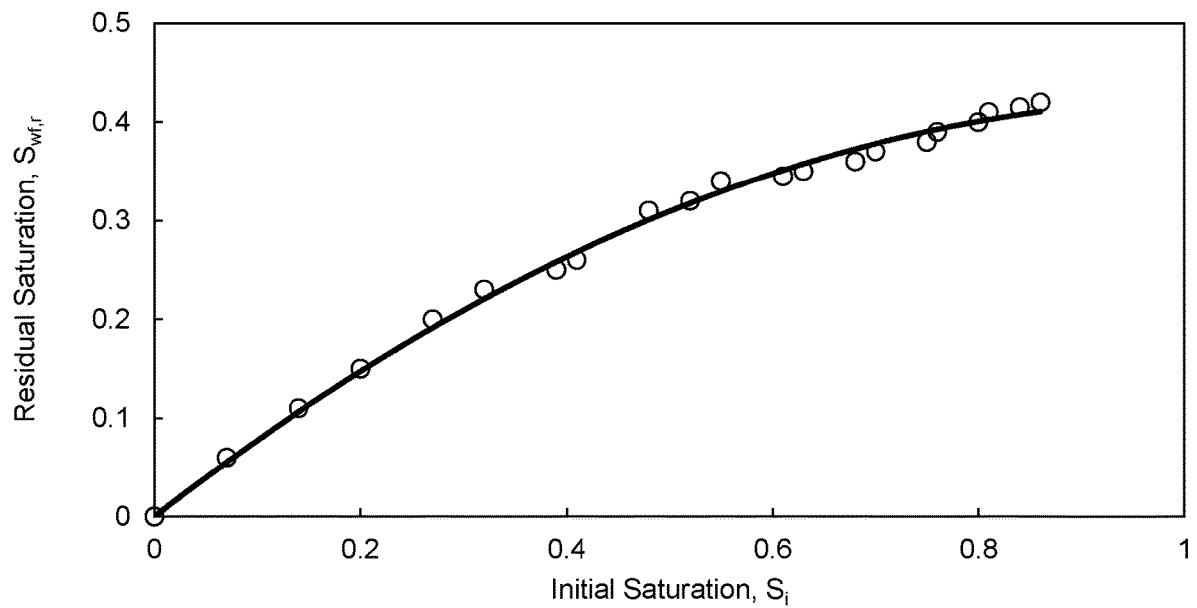
FIG. 7 is a graph showing an initial-residual saturation correlation of the rock sample for water flooding.

FIG. 7 is a graph showing the empirical initial-residual saturation correlation ($S_i$-$S_{wf,r}$) of the rock sample 101 for the water flooding process of step 206 by combining the initial hydrocarbon saturation distribution ($S_i(z)$) shown in FIG. 4 with the water flooding residual hydrocarbon saturation distribution ($S_{wf,r}(z)$) shown in FIG. 6. The empirical initial-residual saturation correlation can also be represented as an equation derived by a best-fit curve of the data (shown as a solid curve in FIG. 7): $S_{wf,r}=-0.392S_i^2+0.8144S_i$. This approach of estimating recoverable hydrocarbon volumes in the oil-water transition zone based on the initial-residual saturation correlation can be more accurate in comparison to traditional methods of estimating such volumes.

The one or more hydrocarbon saturation distributions of the rock sample 101 determined at step 214 can include an EOR flooding residual hydrocarbon saturation distribution, $S_{EORf,r}(z)$. The EOR flooding residual hydrocarbon saturation distribution ($S_{EORf,r}(z)$) can be determined based on the equilibrium sample magnetization distributions measured at step 212a for the EOR flooding process (208) and the core aging process (210). The EOR flooding residual hydrocarbon saturation distribution ($S_{EORf,r}(z)$) can be calculated by Equation 6:

$$S_{EORf,r}(z) = \frac{M_{EORf,r}(z)}{M_o(z)} \quad (6)$$

where $M_{EORf,r}(z)$ is the equilibrium sample magnetization distribution measured for the residual hydrocarbon saturation distribution at the end of the EOR flooding process of step 208.

Figure 8:
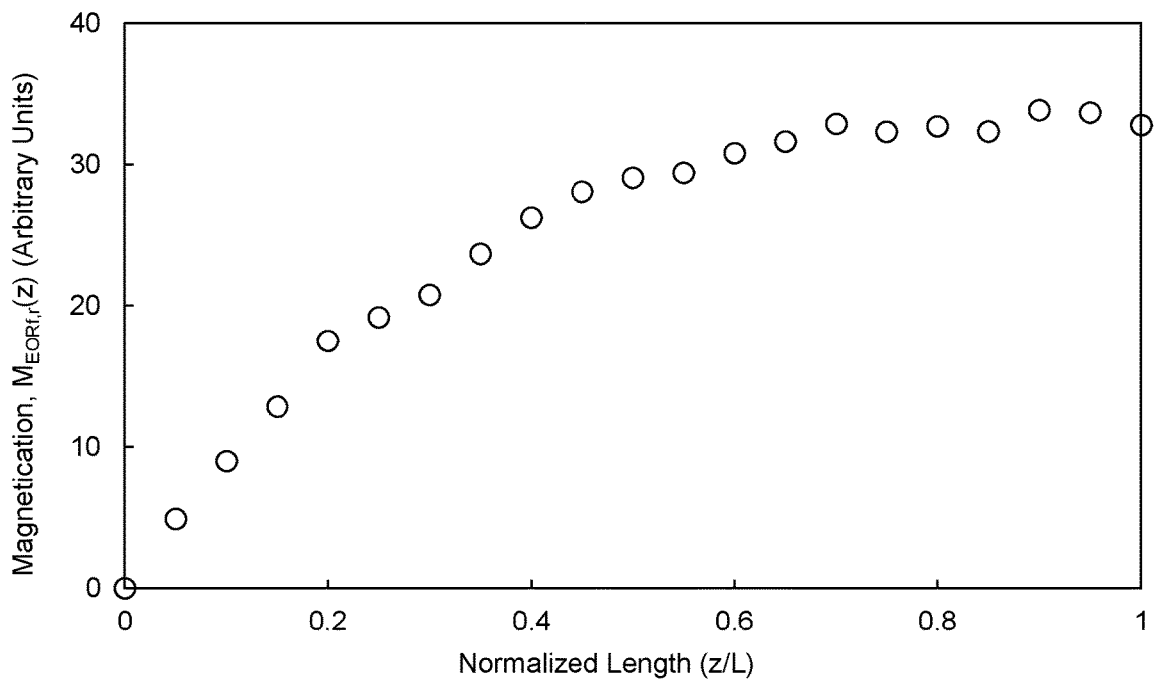
FIG. 8 is a graph showing an equilibrium sample magnetization distribution for an enhanced oil recovery (EOR) flooding residual hydrocarbon saturation distribution along the normalized length of the rock sample.
Figure 9:
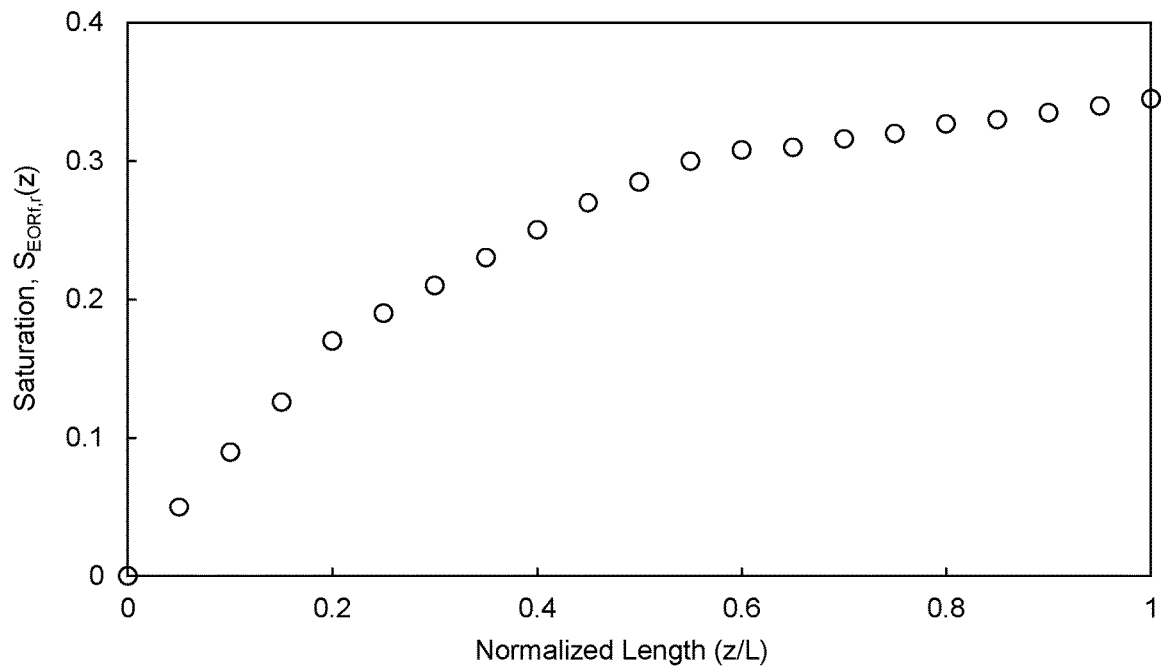
FIG. 9 is a graph showing the EOR flooding residual hydrocarbon saturation distribution along the normalized length of the rock sample.

FIG. 8 is a graph showing the equilibrium sample magnetization distribution $M_{EORf,r}(z)$ for the EOR flooding residual hydrocarbon saturation distribution along the normalized length of the rock sample 101 at the end of the EOR flooding process of step 208. FIG. 9 is a graph showing the EOR flooding residual hydrocarbon saturation distribution ($S_{EORf,r}(z)$, calculated by Equation 6) along the normalized length of the rock sample 101. The amount of hydrocarbons recoverable from the rock sample 101 due to EOR flooding is proportional to the difference between the initial hydrocarbon saturation and the residual hydrocarbon saturation for the EOR flooding process. FIG. 9 shows that EOR flooding residual hydrocarbon saturation in the oil column (where z/L=1) is 0.345 and that residual hydrocarbon saturation in the transition zone decreases gradually with depth. Again, this confirms that the amount of recoverable hydrocarbons and hydrocarbon reserves in the transition zone can potentially be underestimated by traditional methods.

Figure 10:
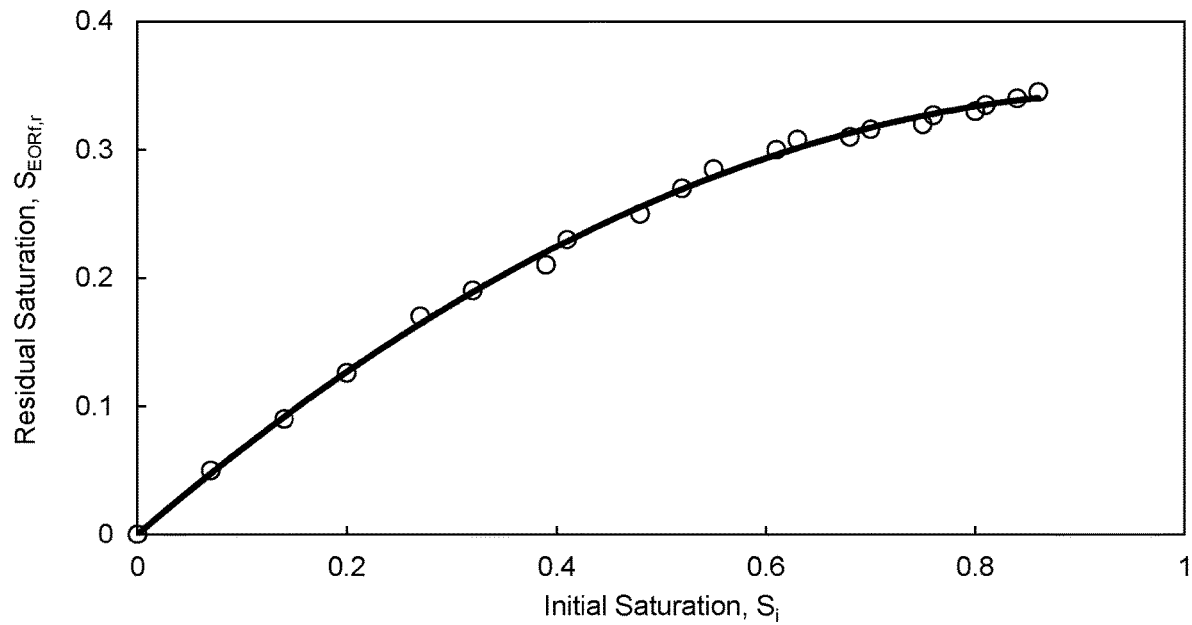
FIG. 10 is a graph showing an initial-residual saturation correlation of the rock sample for EOR flooding.

The empirical initial-residual saturation correlation for the EOR flooding process (208) can be established by combining initial hydrocarbon saturation distribution ($S_i(z)$) with the EOR flooding residual hydrocarbon saturation distribution ($S_{EORf,r}(z)$). For example, individual saturation values can be compared for the same location z along the longitudinal length L of the rock sample 101. FIG. 10 is a graph showing the empirical initial-residual saturation correlation ($S_i$-$S_{EORf,r}$) of the rock sample 101 for the EOR flooding process of step 208 by combining the initial hydrocarbon saturation distribution ($S_i(z)$) shown in FIG. 4 with the EOR flooding residual hydrocarbon saturation distribution ($S_{EORf,r}(z)$) shown in FIG. 9. The empirical initial-residual saturation correlation can also be represented as an equation derived by a best-fit curve of the data (shown as a solid curve in FIG. 10): $S_{EORf,r}=-0.3589S_i^2+0.7044S_i$. This approach of estimating recoverable hydrocarbon volumes in the oil-water transition zone based on the initial-residual saturation correlation can be more accurate in comparison to traditional methods of estimating such volumes.

At step 216, one or more wettability distributions of the rock sample 101 are determined based on the spatially resolved spin-spin relaxation time spectrums measured at step 212b and the one or more hydrocarbon saturation distributions determined at step 214. The one or more wettability distributions of the rock sample 101 determined at step 216 can include an initial hydrocarbon wettability distribution, $W_i(z)$. The initial hydrocarbon wettability distribution ($W_i(z)$) can be determined based on the spatially resolved spin-spin relaxation time spectrum measured at step 212b for the core aging process (204), the spatially resolved spin-spin relaxation time spectrum measured at step 212b for the second core aging process of the core cleaning process (210), and the initial hydrocarbon saturation distribution ($S_i(z)$) determined at step 214. The initial hydrocarbon wettability distribution ($W_i(z)$) can be calculated by Equation 7:

$$W_i(z) = \frac{\left[\frac{1}{T_{2,i}(z)} - \frac{1}{T_{2,B}}\right] S_i(z)}{\frac{1}{T_{2,1}(z)} - \frac{1}{T_{2,B}}} \quad (7)$$

where $T_{2,i}(z)$ is the spatially resolved spin-spin relaxation time spectrum measured at step 212b for the core aging process (204), $T_{2,1}(z)$ is the spatially resolved spin-spin relaxation time spectrum measured at step 212b for the second core aging process of the core cleaning process (210), and $T_{2,B}$ is a bulk spin-spin relaxation time of the hydrocarbon stream.

Figure 11:
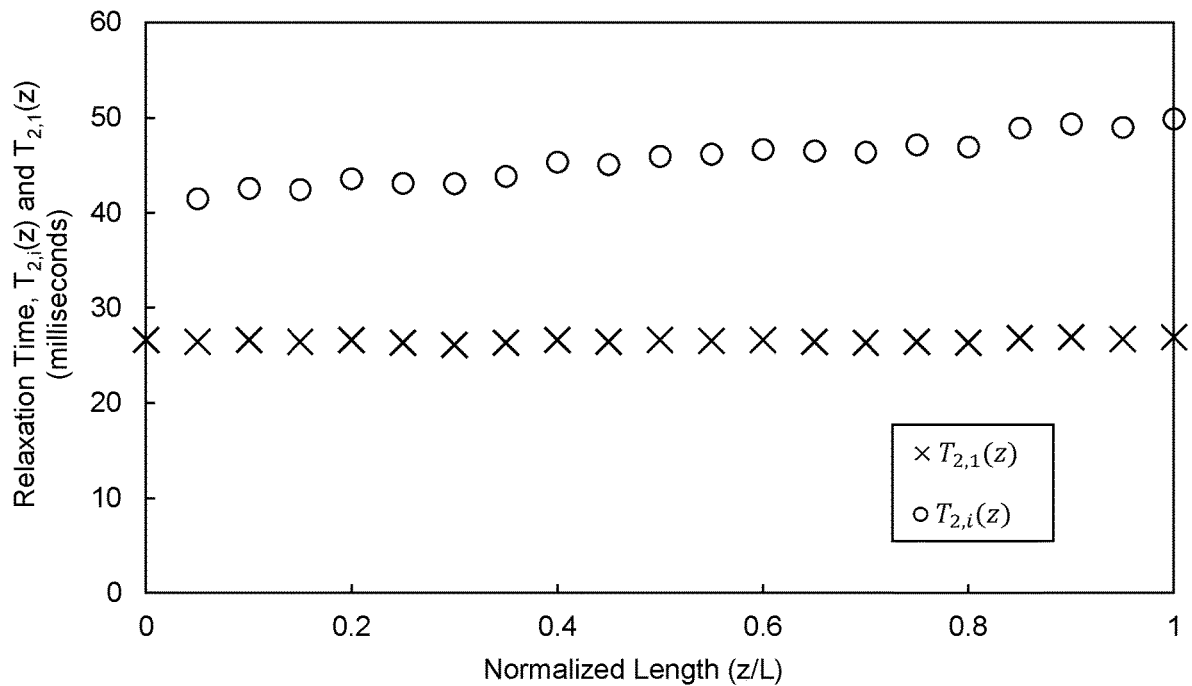
FIG. 11 is a graph showing peak values of spatially resolved spin-spin relaxation time spectra along the normalized length of the rock sample.
Figure 12:
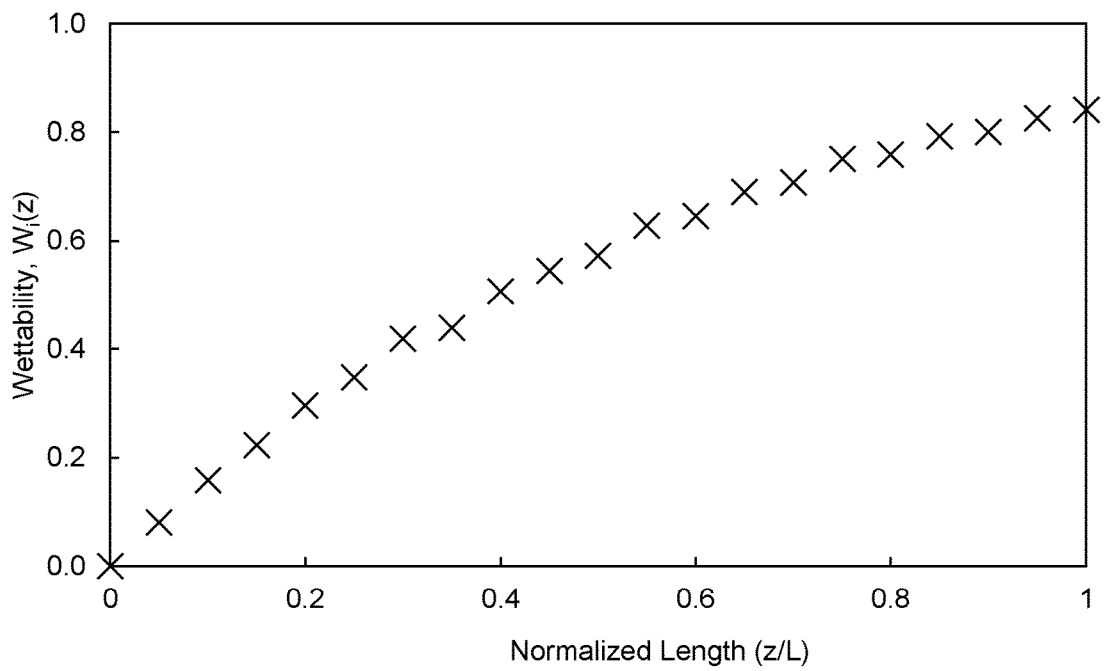
FIG. 12 is a graph showing an initial hydrocarbon wettability distribution along the normalized length of the rock sample.

The peak value of the bulk spin-spin relaxation time spectrum of the hydrocarbon stream was 60 milliseconds (ms). FIG. 11 is a graph showing peak values ($T_{2,i}(z)$) of the spatially resolved spin-spin relaxation time spectrum along the normalized length of the rock sample 101 measured at step 212b for the core aging process of step 204. FIG. 11 also shows peak values ($T_{2,1}(z)$) of the spatially resolved spin-spin relaxation time spectrum along the normalized length of the rock sample 101 measured at step 212b for the second core aging process of step 210. FIG. 12 is a graph showing an initial hydrocarbon wettability distribution ($W_i(z)$, calculated by Equation 7) along the normalized length of the rock sample 101.

The one or more wettability distributions of the rock sample 101 determined at step 216 can include a water flooding residual hydrocarbon wettability distribution, $W_{wf,r}(z)$. The water flooding residual hydrocarbon wettability distribution ($W_{wf,r}(z)$) can be determined based on the spatially resolved spin-spin relaxation time spectrums measured at step 212b for the water flooding process (206) and the second core aging process of the core cleaning process (210) and the water flooding residual hydrocarbon saturation distribution ($S_{wf,r}(z)$) determined at step 214. The water flooding residual hydrocarbon wettability distribution ($W_{wf,r}(z)$) can be calculated by Equation 8:

$$W_{wf,r}(z) = \frac{\left[\frac{1}{T_{2,wf}(z)} - \frac{1}{T_{2,B}}\right]S_{wf,r}(z)}{\frac{1}{T_{2,1}(z)} - \frac{1}{T_{2,B}}} \quad (8)$$

where $T_{2,wf}(z)$ is the spatially resolved spin-spin relaxation time spectrum measured at step 212b for the water flooding process (206).

Figure 13:
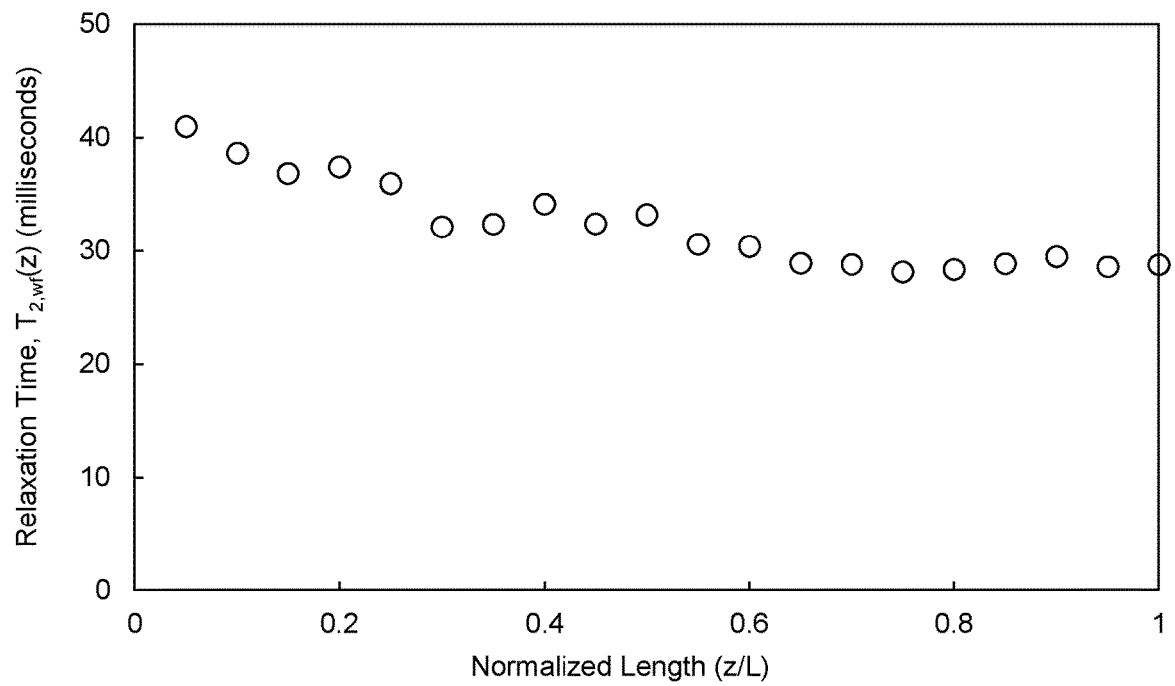
FIG. 13 is a graph showing peak values of spatially resolved spin-spin relaxation time spectra along the normalized length of the rock sample for water flooding.
Figure 14:
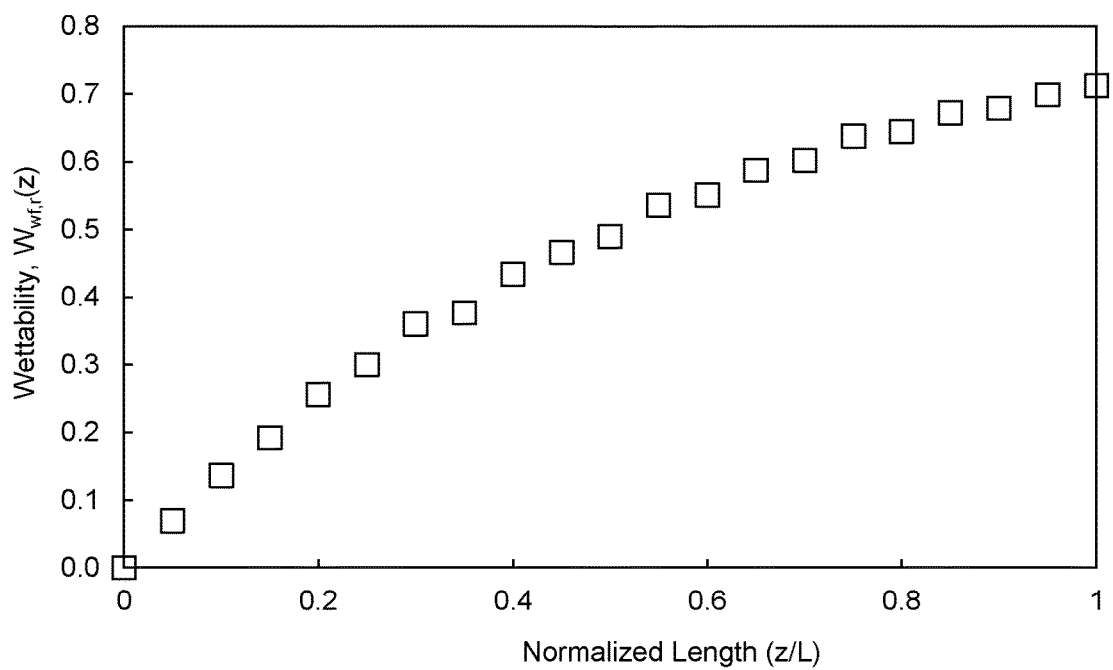
FIG. 14 is a graph showing water flooding residual hydrocarbon wettability distribution along the normalized length of the rock sample.

FIG. 13 is a graph showing peak values ($T_{2,wf}(z)$) of the spatially resolved spin-spin relaxation time spectra along the normalized length of the rock sample 101 measured at step 212b for the water flooding process of step 206. FIG. 14 is a graph showing water flooding residual hydrocarbon wettability distribution ($W_{wf,r}(z)$, calculated by Equation 8) along the normalized length of the rock sample 101.

The one or more wettability distributions of the rock sample 101 determined at step 216 can include an EOR flooding residual hydrocarbon wettability distribution, $W_{EORf,r}(z)$. The EOR flooding residual hydrocarbon wettability distribution ($W_{EORf,r}(z)$) can be determined based on the spatially resolved spin-spin relaxation time spectrums measured at step 212b for the EOR flooding process (208) and the second core aging process of the core cleaning process (210) and the EOR flooding residual hydrocarbon saturation distribution ($S_{EORf,r}(z)$) determined at step 214. The EOR flooding residual hydrocarbon wettability distribution ($W_{EORf,r}(z)$) can be calculated by Equation 9:

$$W_{EORf,r}(z) = \frac{\left[\frac{1}{T_{2,EORf}(z)} - \frac{1}{T_{2,B}}\right]S_{EORf,r}(z)}{\frac{1}{T_{2,1}(z)} - \frac{1}{T_{2,B}}} \quad (9)$$

where $T_{2,EORf}(z)$ is the spatially resolved spin-spin relaxation time spectrum measured at step 212b for the EOR flooding process (208).

Figure 15:
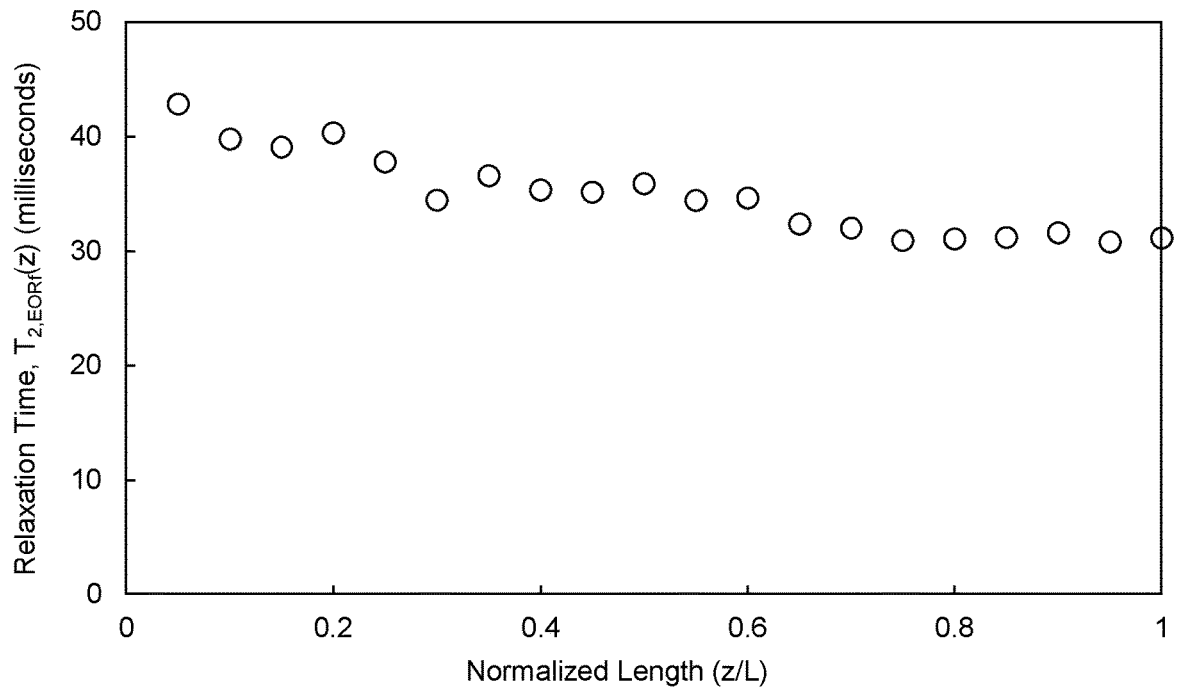
FIG. 15 is a graph showing peak values of spatially resolved spin-spin relaxation time spectra along the normalized length of the rock sample for EOR flooding.
Figure 16:
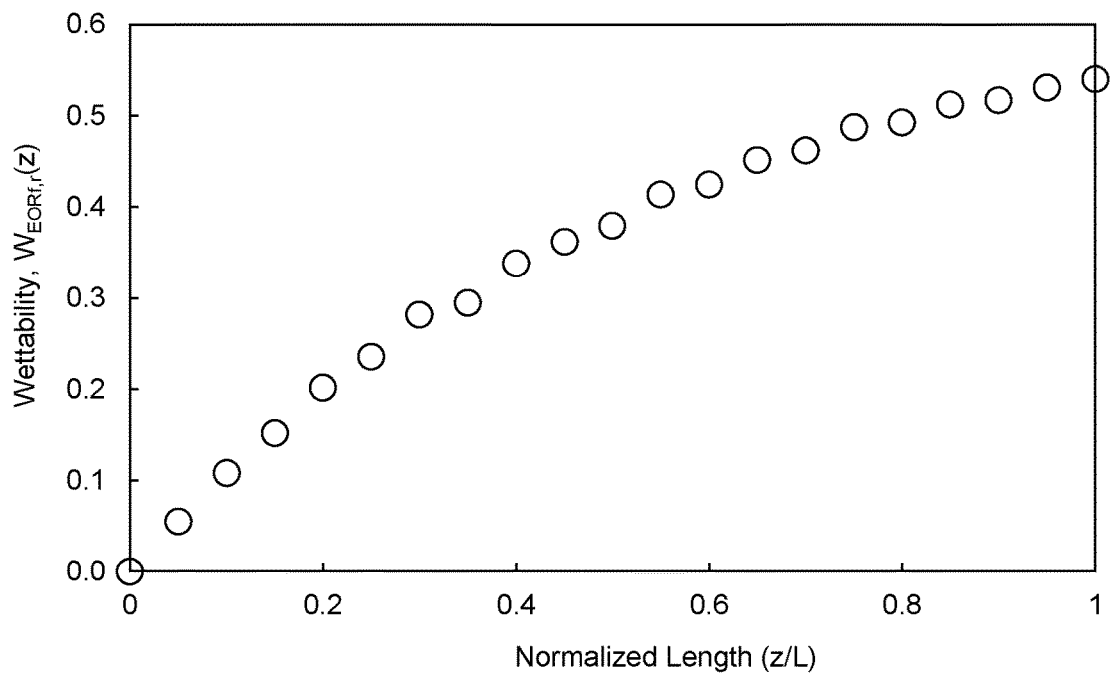
FIG. 16 is a graph showing EOR flooding residual hydrocarbon wettability distribution along the normalized length of the rock sample.

FIG. 15 is a graph showing peak values ($T_{2,EORf}(z)$) of the spatially resolved spin-spin relaxation time spectra along the normalized length of the rock sample 101 measured at step 212b for the EOR flooding process of step 208. FIG. 16 is a graph showing EOR flooding residual hydrocarbon wettability distribution ($W_{EORf,r}(z)$, calculated by Equation 9) along the normalized length of the rock sample 101.

Each value of the initial hydrocarbon wettability distribution ($W_i(z)$), water flooding residual hydrocarbon wettability distribution ($W_{wf,r}(z)$), and EOR flooding residual hydrocarbon wettability distribution ($W_{EORf,r}(z)$) can range between 0 and 1, where 0 represents strongly water wet (that is, water wetting), 1 represents strongly hydrocarbon wet (that is, hydrocarbon wetting), and 0.5 represents equally water and hydrocarbon wet. The wettability of the rock sample 101 may not be uniform along the longitudinal length of the rock sample 101, so the wettability values can depend on the location along the longitudinal length of the rock sample 101.

At step 218, one or more wettability modification factor distributions of the rock sample 101 are determined based on the spatially resolved spin-spin relaxation time spectrums measured at step 212b and the one or more hydrocarbon saturation distributions determined at step 214. The one or more wettability modification factor distributions of the rock sample 101 determined at step 218 can include a water flooding wettability modification factor distribution, $WMF_{wf}(z)$. The water flooding wettability modification factor distribution ($WMF_{wf}(z)$) can be determined based on the spatially resolved spin-spin relaxation time spectrums measured at step 212b for the core aging process (204) and the water flooding process (206), the initial hydrocarbon saturation distribution ($S_i(z)$) determined at step 214, and the water flooding residual hydrocarbon saturation distribution ($S_{wf,r}(z)$) determined at step 214. The water flooding wettability modification factor distribution ($WMF_{wf}(z)$) can be calculated by Equation 10:

$$WMF_{wf}(z) = \frac{\left[\frac{1}{T_{2,wf}(z)} - \frac{1}{T_{2,B}}\right]S_{wf,r}(z)}{\left[\frac{1}{T_{2,i}(z)} - \frac{1}{T_{2,B}}\right]S_i(z)} \quad (10)$$

Figure 17:
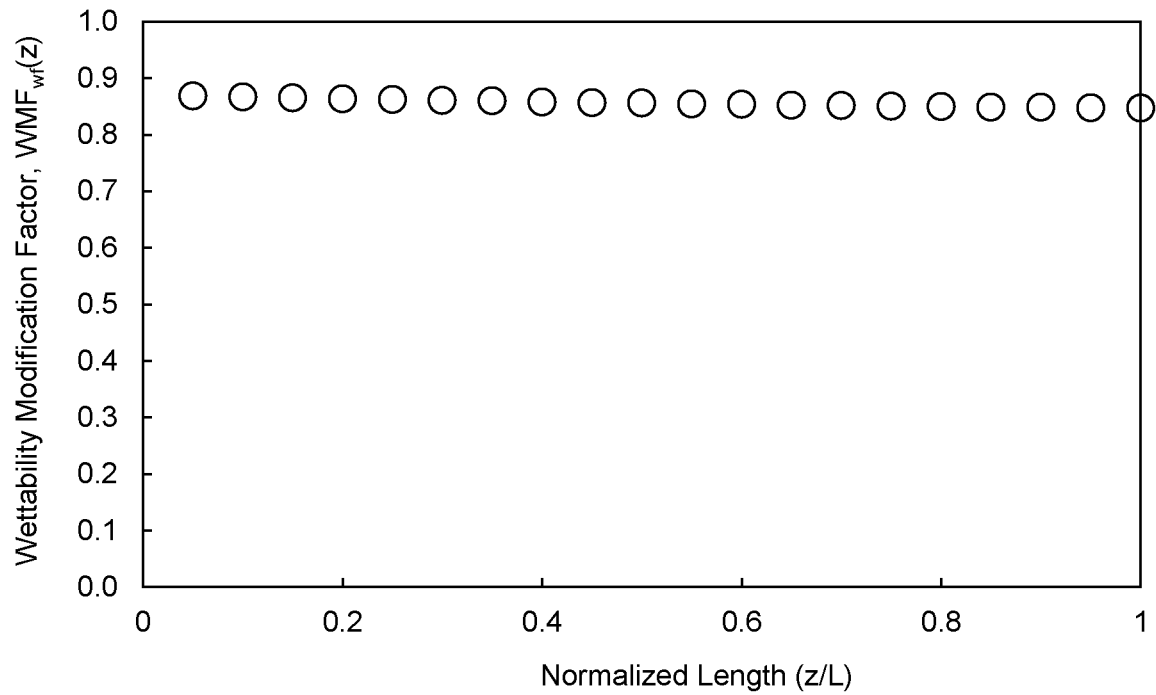
FIG. 17 is a graph showing water flooding wettability modification factor distribution along the normalized length of the rock sample.

FIG. 17 is a graph showing the water flooding wettability modification factor distribution ($WMF_{wf}(z)$, calculated by Equation 10) along the normalized length of the rock sample 101.

The one or more wettability modification factor distributions of the rock sample 101 determined at step 218 can include an EOR flooding wettability modification factor distribution, $WMF_{EORf}(z)$. The EOR flooding wettability modification factor distribution $WMF_{EORf}(z)$) can be determined based on the spatially resolved spin-spin relaxation time spectrums measured at step 212b for the water flooding process (206) and the EOR flooding process (208), the water flooding residual hydrocarbon saturation distribution ($S_{wf,r}(z)$) determined at step 214, and the EOR flooding residual hydrocarbon saturation distribution ($S_{EORf,r}(z)$) determined at step 214. The EOR flooding wettability modification factor distribution ($WMF_{EORf}(z)$) can be calculated by Equation 11:

$$WMF_{EORf}(z) = \frac{\left[\dfrac{1}{T_{2,EORf}(z)} - \dfrac{1}{T_{2,B}}\right] S_{EORf,r}(z)}{\left[\dfrac{1}{T_{2,wf}(z)} - \dfrac{1}{T_{2,B}}\right] S_{wf,r}(z)} \quad (11)$$

Figure 18:
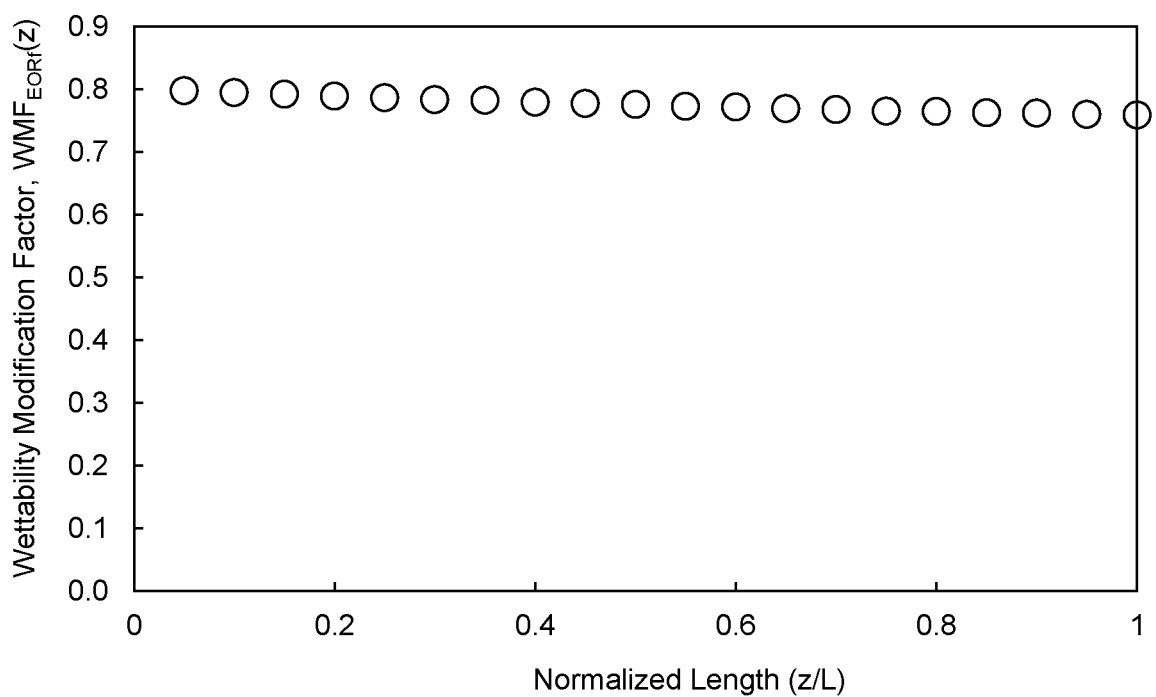
FIG. 18 is a graph showing EOR flooding wettability modification factor distribution along the normalized length of the rock sample.

FIG. 18 is a graph showing the EOR flooding wettability modification factor distribution (WMF$_{EORf}$(z), calculated by Equation 11) along the normalized length of the rock sample 101.

Each value of the water flooding wettability modification factor distribution (WMF$_{EORf}$(z)) and EOR flooding wettability modification factor distribution (WMF$_{EORf}$ (z)) can represent a change in wettability due to the water flooding process (206) and the EOR flooding process (208), respectively. A wettability modification factor value of 1 represents that the wettability did not change as a result of the respective flooding process. A wettability modification factor value of less than 1 represents a shift in wettability toward water wet (that is, the surface became more water wetting) as a result of the respective flooding process. A wettability modification factor value of greater than 1 represents a shift in wettability toward hydrocarbon wet (that is, the surface became more hydrocarbon wetting) as a result of the respective flooding process. The change in wettability of the rock sample 101 may not be uniform along the longitudinal length of the rock sample 101, so the wettability modification factor values can depend on the location along the longitudinal length of the rock sample 101.

Figure 19:
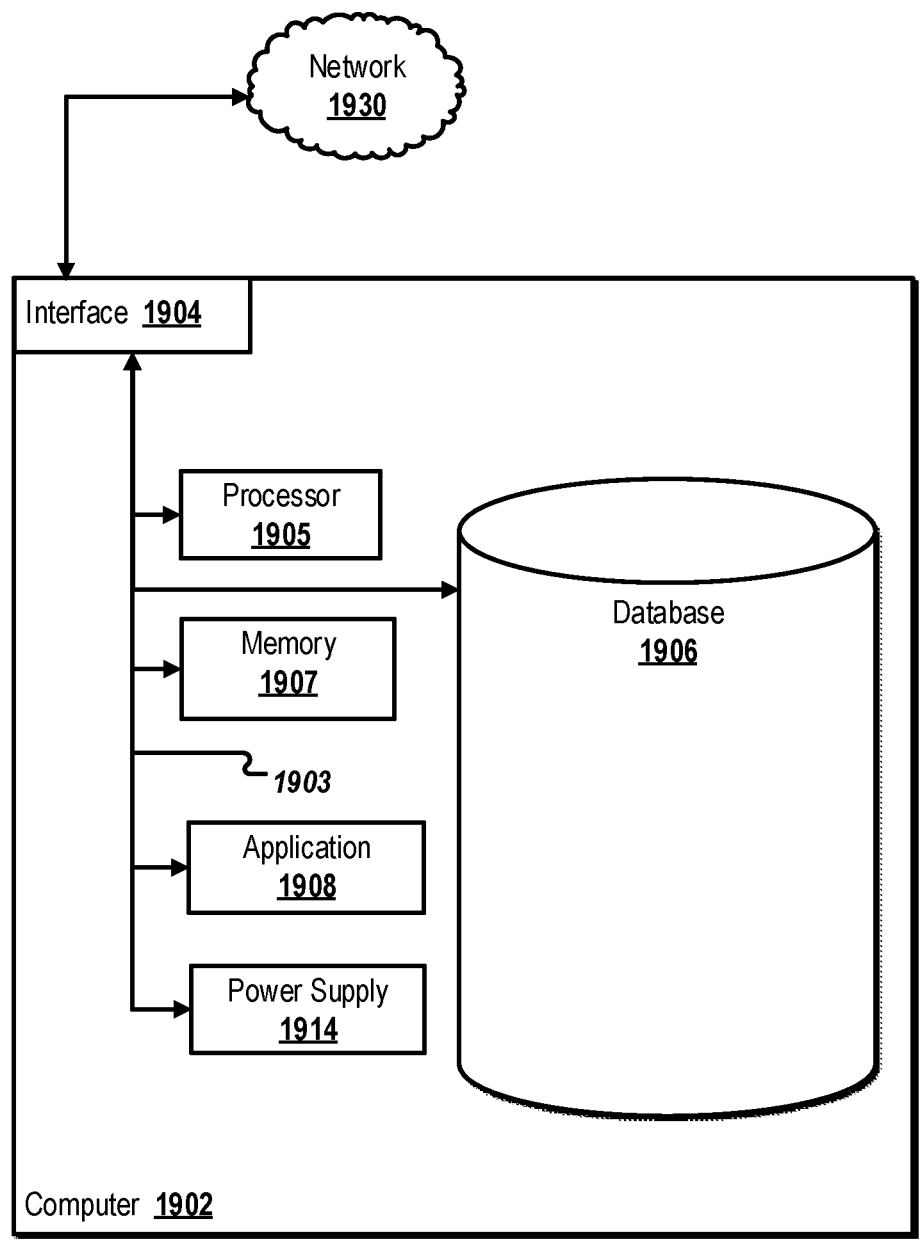
FIG. 19 is a block diagram illustrating an example computer system that can be used to provide computational functionalities associated with described algorithms, methods, functions, processes, flows, and procedures as described in the present disclosure.

FIG. 19 is a block diagram of an example computer system 1900 that can be used to provide computational functionalities associated with described algorithms, methods, functions, processes, flows, and procedures described in the present disclosure, according to some implementations of the present disclosure. For example, the computer system 1900 can be used to automate method 200. For example, the computer system 1900 can be used to perform the calculations associated with Equations 1-11. For example, the computer system 1900 can be used to store the calculated values. The illustrated computer 1902 is intended to encompass any computing device such as a server, a desktop computer, a laptop/notebook computer, a wireless data port, a tablet computing device, or one or more processors within these devices, including physical instances, virtual instances, or both. The computer 1902 can include input devices such as keypads, keyboards, and touch screens that can accept user information. Also, the computer 1902 can include output devices that can convey information associated with the operation of the computer 1902. The information can include digital data, visual data, audio information, or a combination of information. The information can be presented in a graphical user interface (UI) (or GUI).

The computer 1902 can serve in a role as a client, a network component, a server, a database, a persistency, or components of a computer system for performing the subject matter described in the present disclosure. The illustrated computer 1902 is communicably coupled with a network 1930. In some implementations, one or more components of the computer 1902 can be configured to operate within different environments, including cloud-computing-based environments, local environments, global environments, and combinations of environments.

At a high level, the computer 1902 is an electronic computing device operable to receive, transmit, process, store, and manage data and information associated with the described subject matter. According to some implementations, the computer 1902 can also include, or be communicably coupled with, an application server, an email server, a web server, a caching server, a streaming data server, or a combination of servers.

The computer 1902 can receive requests over network 1930 from a client application (for example, executing on another computer 1902). The computer 1902 can respond to the received requests by processing the received requests using software applications. Requests can also be sent to the computer 1902 from internal users (for example, from a command console), external (or third) parties, automated applications, entities, individuals, systems, and computers.

Each of the components of the computer 1902 can communicate using a system bus 1903. In some implementations, any or all of the components of the computer 1902, including hardware or software components, can interface with each other or the interface 1904 (or a combination of both), over the system bus 1903. Interfaces can use an application programming interface (API), a service layer, or a combination of the API and service layer.

The computer 1902 includes an interface 1904. Although illustrated as a single interface 1904 in FIG. 19, two or more interfaces 1904 can be used according to particular needs, desires, or particular implementations of the computer 1902 and the described functionality. The interface 1904 can be used by the computer 1902 for communicating with other systems that are connected to the network 1930 (whether illustrated or not) in a distributed environment. Generally, the interface 1904 can include, or be implemented using, logic encoded in software or hardware (or a combination of software and hardware) operable to communicate with the network 1930. More specifically, the interface 1904 can include software supporting one or more communication protocols associated with communications. As such, the network 1930 or the interface's hardware can be operable to communicate physical signals within and outside of the illustrated computer 1902.

The computer 1902 includes a processor 1905. Although illustrated as a single processor 1905 in FIG. 19, two or more processors 1905 can be used according to particular needs, desires, or particular implementations of the computer 1902 and the described functionality. Generally, the processor 1905 can execute instructions and can manipulate data to perform the operations of the computer 1902, including operations using algorithms, methods, functions, processes, flows, and procedures as described in the present disclosure.

The computer 1902 can include a database 1906 that can hold data for the computer 1902 and other components connected to the network 1930 (whether illustrated or not). For example, database 1906 can be an in-memory, conventional, or a database storing data consistent with the present disclosure. In some implementations, database 1906 can be a combination of two or more different database types (for example, hybrid in-memory and conventional databases) according to particular needs, desires, or particular implementations of the computer 1902 and the described functionality. Although illustrated as a single database 1906 in FIG. 19, two or more databases (of the same, different, or combination of types) can be used according to particular needs, desires, or particular implementations of the computer 1902 and the described functionality. While database 1906 is illustrated as an internal component of the computer 1902, in alternative implementations, database 1906 can be external to the computer 1902.

The computer 1902 includes a memory 1907 that can hold data for the computer 1902 or a combination of components connected to the network 1930 (whether illustrated or not).

Memory 1907 can store any data consistent with the present disclosure. In some implementations, memory 1907 can be a combination of two or more different types of memory (for example, a combination of semiconductor and magnetic storage) according to particular needs, desires, or particular implementations of the computer 1902 and the described functionality. Although illustrated as a single memory 1907 in FIG. 19, two or more memories 1907 (of the same, different, or combination of types) can be used according to particular needs, desires, or particular implementations of the computer 1902 and the described functionality. While memory 1907 is illustrated as an internal component of the computer 1902, in alternative implementations, memory 1907 can be external to the computer 1902.

The application 1908 can be an algorithmic software engine providing functionality according to particular needs, desires, or particular implementations of the computer 1902 and the described functionality. For example, application 1908 can serve as one or more components, modules, or applications. Further, although illustrated as a single application 1908, the application 1908 can be implemented as multiple applications 1908 on the computer 1902. In addition, although illustrated as internal to the computer 1902, in alternative implementations, the application 1908 can be external to the computer 1902.

The computer 1902 can also include a power supply 1914. The power supply 1914 can include a rechargeable or non-rechargeable battery that can be configured to be either user- or non-user-replaceable. In some implementations, the power supply 1914 can include power-conversion and management circuits, including recharging, standby, and power management functionalities. In some implementations, the power-supply 1914 can include a power plug to allow the computer 1902 to be plugged into a wall socket or a power source to, for example, power the computer 1902 or recharge a rechargeable battery.

There can be any number of computers 1902 associated with, or external to, a computer system containing computer 1902, with each computer 1902 communicating over network 1930. Further, the terms "client," "user," and other appropriate terminology can be used interchangeably, as appropriate, without departing from the scope of the present disclosure. Moreover, the present disclosure contemplates that many users can use one computer 1902 and one user can use multiple computers 1902.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

As used in this disclosure, the term "about" or "approximately" can allow for a degree of variability in a value or range, for example, within 10%, within 5%, or within 1% of a stated value or of a stated limit of a range.

As used in this disclosure, the term "substantially" refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A method comprising:
conducting a primary drainage process on a rock sample;
conducting a core aging process on the rock sample;
conducting a water flooding process on the rock sample;
conducting an enhanced oil recovery (EOR) flooding process on the rock sample;
conducting a core cleaning process on the rock sample;
for each of the primary drainage process, the core aging process, the water flooding process, the EOR flooding process, and the core cleaning process:
measuring an equilibrium sample magnetization distribution across a plurality of locations along a longitudinal length of the rock sample; and
measuring a spatially resolved spin-spin relaxation time spectrum across the plurality of locations along the longitudinal length of the rock sample;
determining one or more hydrocarbon saturation distributions of the rock sample based on the equilibrium sample magnetization distributions;
determining one or more wettability distributions of the rock sample based on the spatially resolved spin-spin relaxation time spectrums and the one or more hydrocarbon saturation distributions; and
determining one or more wettability modification factor distributions of the rock sample based on the spatially resolved spin-spin relaxation time spectrums and the one or more hydrocarbon saturation distributions.

2. The method of claim 1, wherein each of the primary drainage process and the core aging process comprises:
flowing a hydrocarbon stream into a first end of the rock sample at a first hydrocarbon flow rate; and
flowing a deuterium oxide ($D_2O$) stream across a second end of the rock sample at a first $D_2O$ flow rate, wherein the first hydrocarbon flow rate is greater than the first $D_2O$ flow rate, and the flows of the hydrocarbon stream and the $D_2O$ stream to the rock sample results in a differential pressure across the longitudinal length of the rock sample.

3. The method of claim 2, wherein the water flooding process comprises:
flowing the $D_2O$ stream into the second end of the rock sample at a second $D_2O$ flow rate, wherein the second $D_2O$ flow rate is greater than the first $D_2O$ flow rate; and
reducing the flow of the hydrocarbon stream across the first end of the rock sample, wherein the differential pressure across the longitudinal length of the rock sample during the water flooding process is substantially equal to the differential pressure during the primary drainage process.

4. The method of claim 2, wherein the EOR flooding process comprises:
flowing an EOR stream into the second end of the rock sample, wherein the EOR stream has a different composition from the $D_2O$ stream; and
reducing the flow of the hydrocarbon stream across the first end of the rock sample, wherein the differential pressure across the longitudinal length of the rock sample during the EOR flooding process is substantially equal to the differential pressure during the water flooding process.

5. The method of claim 2, wherein the core cleaning process further comprises:
measuring an equilibrium sample magnetization distribution across the plurality of locations along the longitudinal length of the rock sample;
measuring a spatially resolved spin-spin relaxation time spectrum across the plurality of locations along the longitudinal length of the rock sample; and
flowing the hydrocarbon stream through the rock sample until the spatially resolved spin-spin relaxation time spectrum across the plurality of locations along the longitudinal length of the rock sample stabilizes.

6. The method of claim 1, wherein the core cleaning process comprises:
a) flowing toluene through the rock sample;
b) flowing methanol through the rock sample; and
c) repeating and alternating between steps a) and b) until an effluent from the rock sample is visually clear.

7. The method of claim 1, wherein the one or more hydrocarbon saturation distributions comprises an initial hydrocarbon saturation distribution ($S_i(z)$), and determining the one or more hydrocarbon saturation distributions comprises determining the initial hydrocarbon saturation distribution to be a ratio of the equilibrium sample magnetization distribution for the core aging process to the equilibrium sample magnetization distribution for the core cleaning process.

8. The method of claim 7, wherein the one or more hydrocarbon saturation distributions comprises a water flooding residual hydrocarbon saturation distribution ($S_{wf,r}(z)$), and determining the one or more hydrocarbon saturation distributions comprises determining the water flooding residual hydrocarbon saturation distribution to be a ratio of the equilibrium sample magnetization distribution for the water flooding process to the equilibrium sample magnetization distribution for the core cleaning process.

9. The method of claim 8, wherein the one or more hydrocarbon saturation distributions comprises an EOR flooding residual hydrocarbon saturation distribution ($S_{EORf,r}(z)$), and determining the one or more hydrocarbon saturation distributions comprises determining the EOR flooding residual hydrocarbon saturation distribution to be a ratio of the equilibrium sample magnetization distribution for the EOR flooding process to the equilibrium sample magnetization distribution for the core cleaning process.

10. The method of claim 9, wherein the one or more wettability distributions comprises an EOR flooding residual hydrocarbon wettability distribution ($W_{EORf,r}(z)$), and determining the one or more wettability distributions comprises determining the EOR flooding residual hydrocarbon wettability distribution to be:

$$W_{EORf,r}(z) = \frac{\left[\frac{1}{T_{2,EORf}(z)} - \frac{1}{T_{2,B}}\right]S_{EORf,r}(z)}{\frac{1}{T_{2,1}(z)} - \frac{1}{T_{2,B}}},$$

wherein $T_{2,EORf}(z)$ is the spatially resolved spin-spin relaxation time spectrum for the EOR flooding process, $T_{2,1}(z)$ is the spatially resolved spin-spin relaxation time spectrum for the core cleaning process, and $T_{2,B}$ is a bulk spin-spin relaxation time of the hydrocarbon stream.

11. The method of claim 9, wherein the one or more wettability modification factor distributions comprises an EOR wettability modification factor distribution ($WMF_{EORf}(z)$), and determining the one or more wettability modification factor distributions comprises determining the EOR flooding wettability modification factor distribution to be:

$$WMF_{EORf}(z) = \frac{\left[\frac{1}{T_{2,EORf}(z)} - \frac{1}{T_{2,B}}\right]S_{EORf,r}(z)}{\left[\frac{1}{T_{2,wf}(z)} - \frac{1}{T_{2,B}}\right]S_{wf,r}(z)},$$

wherein $T_{2,EORf}(z)$ is the spatially resolved spin-spin relaxation time spectrum for the EOR flooding process, $T_{2,wf}(z)$ is the spatially resolved spin-spin relaxation time spectrum for the water flooding process, and $T_{2,B}$ is a bulk spin-spin relaxation time of the hydrocarbon stream.

12. The method of claim 8, wherein the one or more wettability distributions comprises a water flooding residual hydrocarbon wettability distribution ($W_{wf,r}(z)$), and determining the one or more wettability distributions comprises determining the water flooding residual hydrocarbon wettability distribution to be:

$$W_{wf,r}(z) = \frac{\left[\frac{1}{T_{2,wf}(z)} - \frac{1}{T_{2,B}}\right]S_{wf,r}(z)}{\frac{1}{T_{2,1}(z)} - \frac{1}{T_{2,B}}},$$

wherein $T_{2,wf}(z)$ is the spatially resolved spin-spin relaxation time spectrum for the water flooding process, $T_{2,1}(z)$ is the spatially resolved spin-spin relaxation time spectrum for the core cleaning process, and $T_{2,B}$ is a bulk spin-spin relaxation time of the hydrocarbon stream.

13. The method of claim 8, wherein the one or more wettability modification factor distributions comprises a water flooding wettability modification factor distribution ($WMF_{wf}(z)$), and determining the one or more wettability modification factor distributions comprises determining the water flooding wettability modification factor distribution to be:

$$WMF_{wf}(z) = \frac{\left[\frac{1}{T_{2,wf}(z)} - \frac{1}{T_{2,B}}\right] S_{wf,r}(z)}{\left[\frac{1}{T_{2,i}(z)} - \frac{1}{T_{2,B}}\right] S_i(z)},$$

wherein $T_{2,wf}(z)$ is the spatially resolved spin-spin relaxation time spectrum for the water flooding process, $T_{2,i}(z)$ is the spatially resolved spin-spin relaxation time spectrum for the core aging process, and $T_{2,B}$ is a bulk spin-spin relaxation time of the hydrocarbon stream.

14. The method of claim 7, wherein the one or more wettability distributions comprises an initial hydrocarbon wettability distribution ($W_i(z)$), and determining the one or more wettability distributions comprises determining the initial hydrocarbon wettability distribution to be:

$$W_i(z) = \frac{\left[\frac{1}{T_{2,i}(z)} - \frac{1}{T_{2,B}}\right] S_i(z)}{\frac{1}{T_{2,1}(z)} - \frac{1}{T_{2,B}}},$$

wherein $T_{2,i}(z)$ is the spatially resolved spin-spin relaxation time spectrum for the core aging process, $T_{2,1}(z)$ is the spatially resolved spin-spin relaxation time spectrum for the core cleaning process, and $T_{2,B}$ is a bulk spin-spin relaxation time of the hydrocarbon stream.

* * * * *